(12) United States Patent
Chi et al.

(10) Patent No.: US 10,008,680 B2
(45) Date of Patent: Jun. 26, 2018

(54) IRIDIUM COMPLEX AND NITROGEN-CONTAINING TRIDENTATE LIGAND

(71) Applicant: National Tsing Hua University, Hsinchu (TW)

(72) Inventors: Yun Chi, Hsinchu (TW); Jun Lin, Taoyuan (TW); Pi-Yu Chen, Taoyuan (TW)

(73) Assignee: National Tsing Hua University, Hsinchu (TW)

( * ) Notice: Subject to any disclaimer, the term of this patent is extended or adjusted under 35 U.S.C. 154(b) by 0 days. days.

(21) Appl. No.: 15/234,498

(22) Filed: Aug. 11, 2016

(65) Prior Publication Data
US 2017/0338426 A1 Nov. 23, 2017

(30) Foreign Application Priority Data
May 17, 2016 (TW) .............................. 105115123 A

(51) Int. Cl.
| C07D 401/04 | (2006.01) |
| C07F 15/00 | (2006.01) |
| H01L 51/00 | (2006.01) |
| C09K 11/06 | (2006.01) |
| H01L 51/50 | (2006.01) |

(52) U.S. Cl.
CPC ........ H01L 51/0085 (2013.01); C07D 401/04 (2013.01); C07F 15/0033 (2013.01); C09K 11/06 (2013.01); C09K 2211/1007 (2013.01); C09K 2211/1044 (2013.01); C09K 2211/185 (2013.01); H01L 51/5016 (2013.01)

(58) Field of Classification Search
CPC .. C07D 401/04; C07D 401/14; C07D 403/04; C09K 11/06; H01L 51/50
USPC ............ 428/690; 544/225; 546/2, 27, 272.4, 546/275.4
See application file for complete search history.

(56) References Cited

U.S. PATENT DOCUMENTS

| 2013/0018189 A1 | 1/2013 | Chi et al. |
| 2016/0043331 A1 | 2/2016 | Li et al. |
| 2017/0194575 A1* | 7/2017 | Chi ..................... H01L 51/0085 |

FOREIGN PATENT DOCUMENTS

| CN | 103172676 | 6/2013 |
| TW | 200624436 | 7/2006 |

OTHER PUBLICATIONS

Hsu et al.,"Ru(II) sensitizers with a tridentate heterocyclic cyclometalate for dye-sensitized solar cells", Energy & Environmental Science, May 2012, pp. 7549-7554.
Kuei et al., "Bis-Tridentate Ir(III) Complexes with Nearly Unitary RGB Phosphorescence and Organic Light-Emitting Diodes with External Quantum Efficiency Exceeding 31%", Advanced Materials, Apr. 2016, pp. 2795-2800.
Sanning et al., "Colour-tunable asymmetric cyclometalated Pt(II) complexes and STM-assisted stability assessment of ancillary ligands for OLEDs", Journal of Materials Chemistry C, Apr. 2016, pp. 2560-2565.

(Continued)

*Primary Examiner* — Deepak R Rao
(74) *Attorney, Agent, or Firm* — J.C. Patents

(57) ABSTRACT

An iridium complex and a nitrogen-containing tridentate ligand are provided. The iridium complex is represented by below formula:

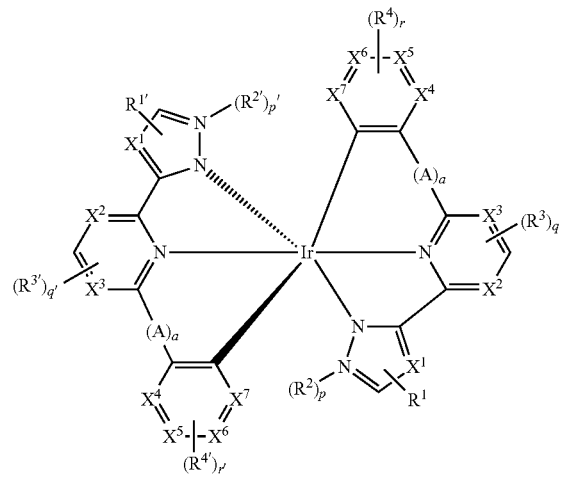

wherein $R^1$ and $R^{1'}$ are each independently substituted or unsubstituted $C_1$-$C_{12}$ alkyl, substituted or unsubstituted $C_6$-$C_{12}$ aryl, or —$C_mF_{2m+1}$, m is an integer of 0 to 3; $R^2$ and $R^{2'}$ are each independently hydrogen, substituted or unsubstituted $C_1$-$C_{12}$ alkyl, or substituted or unsubstituted $C_6$-$C_{12}$ aryl; p and p' are each independently 0 or 1; $R^3$, $R^{3'}$, $R^4$ and $R^{4'}$ are each independently hydrogen, fluorine, substituted or unsubstituted $C_1$-$C_{12}$ alkyl, substituted or unsubstituted $C_1$-$C_6$ alkoxyl, or substituted or unsubstituted $C_6$-$C_{12}$ aryl; q and q' are each independently an integer of 0 to 3; r and r' are each independently an integer of 0 to 4; $X^1$ to $X^7$ are each independently carbon or nitrogen; A is —O—, —$CH_2$—, or —$CR_2$—, R is methyl, ethyl, or propyl; and a is 0 or 1.

15 Claims, 4 Drawing Sheets

(56) References Cited

OTHER PUBLICATIONS

"Office Action of Taiwan Counterpart Application", dated Sep. 8, 2016, p. 1-p. 5.

* cited by examiner

IRIDIUM COMPLEX AND NITROGEN-CONTAINING TRIDENTATE LIGAND

CROSS-REFERENCE TO RELATED APPLICATION

This application claims the priority benefit of Taiwan application serial no. 105115123, filed on May 17, 2016. The entirety of the above-mentioned patent application is hereby incorporated by reference herein and made a part of this specification.

BACKGROUND OF THE INVENTION

Field of the Invention

The invention relates to a metal complex, and more particularly, to an iridium complex suitable for an organic light-emitting diode (OLED) and a nitrogen-containing tridentate ligand suitable for forming the iridium complex.

Description of Related Art

Organic-light emitting diode (OLED) devices have received much attention in the display industry, especially in the flat panel display industry, since the OLED devices can be operated under low driving voltage and can produce high luminous efficiency.

To develop a flat panel display with full color, the development of a color light-emitting material that is easy to synthesize and has high luminous efficiency is the main object of current OLED research. The existing tris-bidentate iridium complex has suitable emission properties, but the rigidity, stability, and ease of synthesis thereof are insufficient.

SUMMARY OF THE INVENTION

The invention provides an iridium complex that has sufficient rigidity and stability, is easy to synthesize, and has different valence states or different charges on the complex.

The invention also provides a nitrogen-containing tridentate ligand suitable for forming the iridium complex.

The iridium complex of the invention is represented by general formula (I):

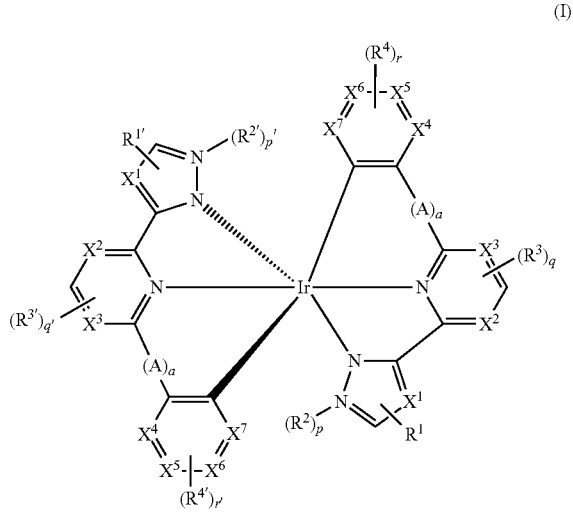

(I)

wherein $R^1$ and $R^{1'}$ are each independently substituted or unsubstituted $C_1$-$C_{12}$ alkyl, substituted or unsubstituted $C_6$-$C_{12}$ aryl, or —$C_mF_{2m+1}$, m is an integer of 0 to 3; $R^2$ and $R^{2'}$ are each independently hydrogen, substituted or unsubstituted $C_1$-$C_{12}$ alkyl, or substituted or unsubstituted $C_6$-$C_{12}$ aryl; p and p' are each independently 0 or 1; $R^3$, $R^{3'}$, $R^4$ and $R^{4'}$ are each independently hydrogen, fluorine, substituted or unsubstituted $C_1$-$C_{12}$ alkyl, substituted or unsubstituted $C_1$-$C_6$ alkoxyl, or substituted or unsubstituted $C_6$-$C_{12}$ aryl; q and q' are each independently an integer of 0 to 3; r and r' are each independently an integer of 0 to 4; $X^1$, $X^2$, $X^3$, $X^4$, $X^5$, $X^6$, and $X^7$ are each independently carbon or nitrogen; A is —O—, —$CH_2$—, or —$CR_2$—, R is methyl, ethyl, or propyl; a is 0 or 1; when q is equal to or greater than 2, each $R^3$ can be the same or different, and two or more $R^3$'s can joint to form a $C_3$-$C_8$ aromatic ring; when q' is equal to or greater than 2, each $R^{3'}$ can be the same or different, and two or more $R^{3'}$'s can joint to form a $C_3$-$C_8$ aromatic ring; when r is equal to or greater than 2, each $R^4$ can be the same or different, and two or more $R^4$'s can joint to form a $C_3$-$C_8$ aromatic ring; and when r' is equal to or greater than 2, each $R^{4'}$ can be the same or different, and two or more $R^{4'}$'s can joint to form a $C_3$-$C_8$ aromatic ring.

The nitrogen-containing tridentate ligand of the invention is represented by general formula (II):

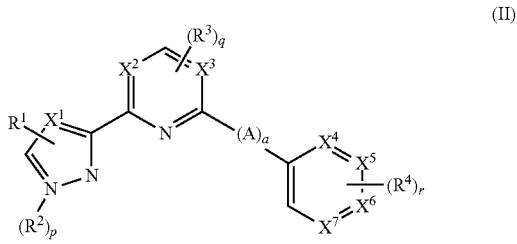

(II)

wherein $R^1$ to $R^4$, $X^1$ to $X^7$, p, q, r, A, and a are as defined in general formula (I).

The bis-tridentate iridium complex of the invention has strong rigidity and high stability, and can therefore increase luminous efficiency. The iridium complex of the invention is easily synthesized, is convenient to purify, and has a high synthetic yield, and is therefore suitable for commercial production. Moreover, the structure of the iridium complex of the invention can also be modified via a simple reaction to change the valence state or the formal charge on the final complex thereof. The iridium complex having a neutral valence state can be used in fabrication of OLED using thermal vacuum deposition. The iridium complex having a positive or negative charge is potentially water-soluble and can be modified with biological functional groups, and accordingly can be applied in the medical field. Therefore, the application of the iridium complex of the invention is very broad.

In order to present the advantages of the aforementioned features and disclosure more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
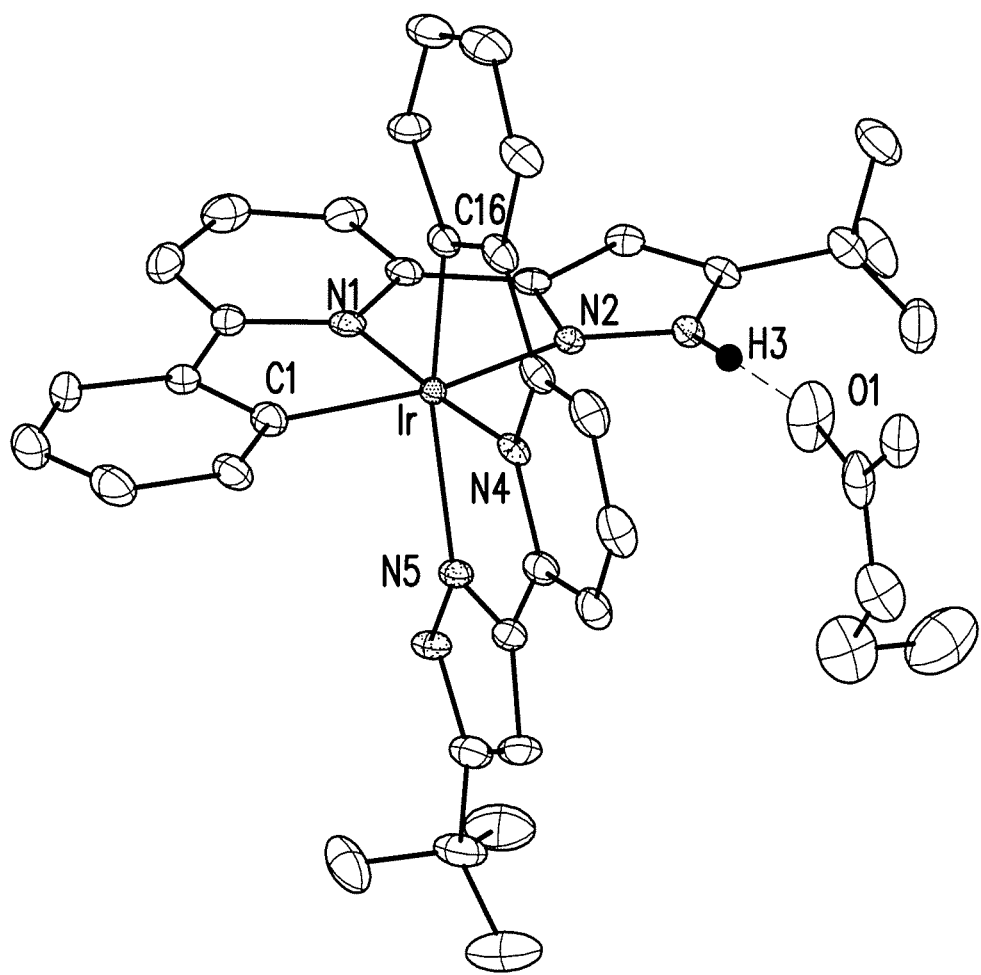
FIG. 1 shows a single crystal X-ray diffraction pattern of compound (I-1) synthesized in example 1 of the invention.

In the following, embodiments are provided to further describe the invention, but the embodiments are only exemplary and are not intended to limit the scope of the invention.

[Structure of Iridium Complex]

The structure of the iridium complex of the invention is represented by general formula (I):

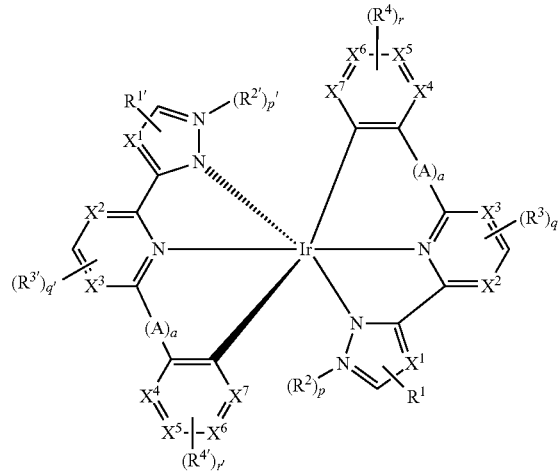

wherein $R^1$ and $R^{1'}$ are each independently substituted or unsubstituted $C_1$-$C_{12}$ alkyl, substituted or unsubstituted $C_6$-$C_{12}$ aryl, or —$C_mF_{2m+1}$, m is an integer of 0 to 3; $R^2$ and $R^{2'}$ are each independently hydrogen, substituted or unsubstituted $C_1$-$C_{12}$ alkyl, or substituted or unsubstituted $C_6$-$C_{12}$ aryl; p and p' are each independently 0 or 1; $R^3$, $R^{3'}$, $R^4$ and $R^{4'}$ are each independently hydrogen, fluorine, substituted or unsubstituted $C_1$-$C_{12}$ alkyl, substituted or unsubstituted $C_1$-$C_6$ alkoxyl, or substituted or unsubstituted $C_6$-$C_{12}$ aryl; q and q' are each independently an integer of 0 to 3; r and r' are each independently an integer of 0 to 4; $X^1$ to $X^7$ are each independently carbon or nitrogen; A is —O—, —$CH_2$—, or —$CR_2$—, R is methyl, ethyl, or propyl; and a is 0 or 1.

In general formula (I), when q is equal to or greater than 2, each $R^3$ can be the same or different, and two or more $R^3$'s can joint to form a $C_3$-$C_8$ aromatic ring. Similarly, when q' is equal to or greater than 2, each $R^{3'}$ can be the same or different, and two or more $R^{3'}$'s can joint to form a $C_3$-$C_8$ aromatic ring. When r is equal to or greater than 2, each $R^4$ can be the same or different, and two or more $R^4$'s can joint to form a $C_3$-$C_8$ aromatic ring. When r' is equal to or greater than 2, each $R^{4'}$ can be the same or different, and two or more $R^{4'}$'s can joint to form a $C_3$-$C_8$ aromatic ring.

The aromatic entity include aromatic hydrocarbon or heterocyclic entity. Specific examples of the aromatic entity include benzene, pyridine, pyrazine, pyrimidine, pyridazine, triazine, pyrrole, furan, thiophene, selenophene, tellurophene, imidazole, thiazole, selenazole, tellurazole, thiadiazole, oxadiazole, pyrazole and etc.

It is noted that, proton transfer occurs to the ligand precursor during the synthesis of the iridium complex of the invention. Therefore, even if only a single type of ligand precursor is used for the reaction, the ligands on the iridium complex of the invention can carry different formal charges and form an electrically neutral complex with an iridium (III) metal.

For instance, as shown in the figure below, both cyclometalation and proton transfer occur to a ligand precursor of the invention to form a monoanionic ligand.

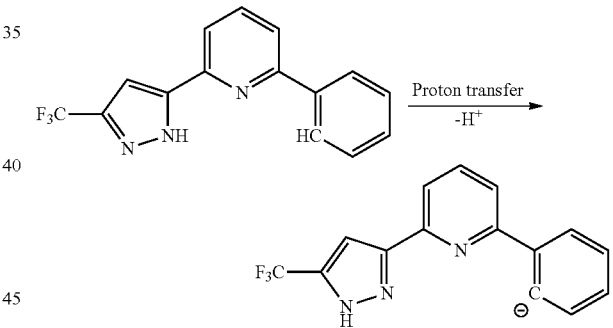

Moreover, proton transfer does not occur at pyrazolyl fragment of the invention, and both cyclometalation and deprotonation of pyrazole are occurred to form a negative dianionic ligand.

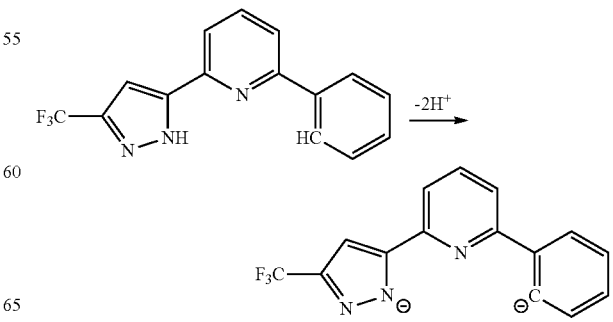

The dianionic ligand and the monoanionic ligand form an electrically charge-neutral iridium complex of the invention with the iridium metal atom at 3+ oxidation state.

In an embodiment, a bonding site of $R^{1'}$ of the left ligand is the same as a bonding site of $R^1$ of the right ligand, and $R^{1'}$ and $R^1$ have the same structure; a bonding site of $R^{3'}$ of the left ligand is the same as a bonding site of $R^3$ of the right ligand, and $R^{3'}$ and $R^3$ have the same structure; and a bonding site of $R^{4'}$ of the left ligand is the same as a bonding site of $R^4$ of the right ligand, and $R^{4'}$ and $R^4$ have the same structure.

In an embodiment, the iridium complex of the invention is a homoleptic complex. That is, the structures of the right ligand and the left ligand of the iridium complex of the invention are completely identical. More specifically, in general formula (I), the structures of $R^1$, $R^3$, and $R^4$ on the right ligand and $R^{1'}$, $R^{3'}$, and $R^{4'}$ on the left ligand are the same and the bonding sites thereof are the same. However, the invention is not limited thereto.

In another embodiment, in general formula (I), the structures and/or bonding sites of $R^1$, $R^3$, and $R^4$ on the right ligand and $R^{1'}$, $R^{3'}$, and $R^{4'}$ on the left ligand can be different to form an asymmetric heteroleptic complex.

In an embodiment, when a is 0, the two ligands on the iridium complex respectively have a complete conjugate structure.

The structure of the iridium complex of the invention can be modified via a simple reaction to change the valence state or formal charge on complex thereof.

In an embodiment, the iridium complex is electrically neutral. More specifically, in general formula (I), one of p and p' is 1, the other of p and p' is 0, and the structures thereof can be represented by any one of formula (I-1) to formula (I-32) and formula (I-32-a) to formula (I-32-b):

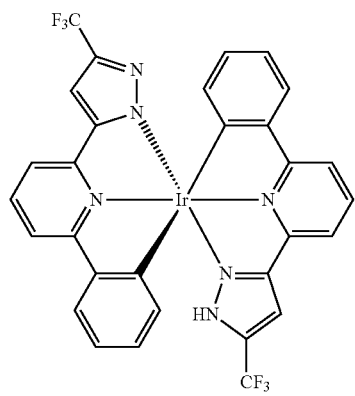

I-1

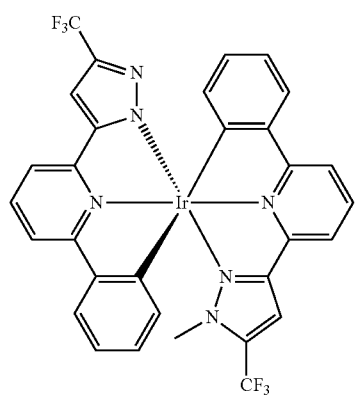

I-2

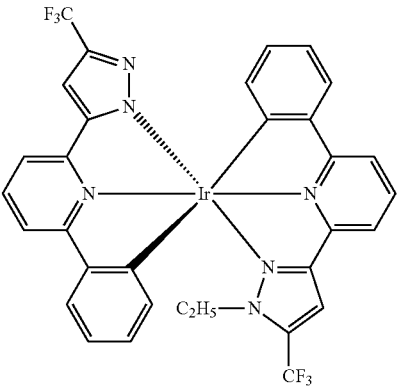

I-3

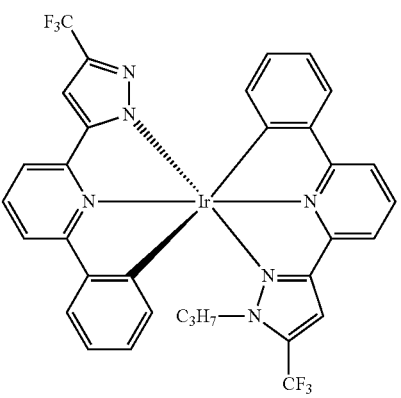

I-4

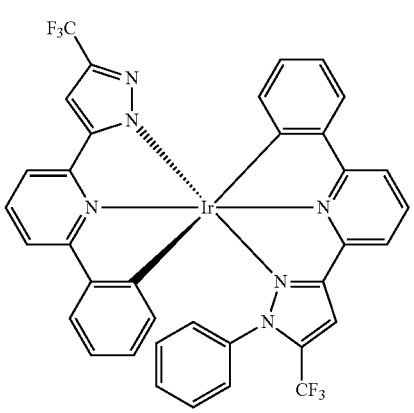

I-5

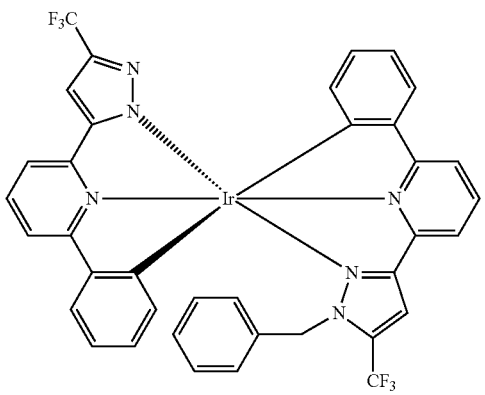

I-6

-continued
I-7
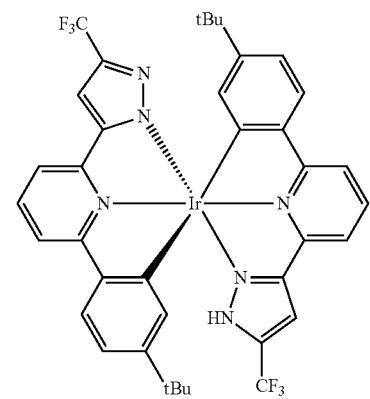
I-8
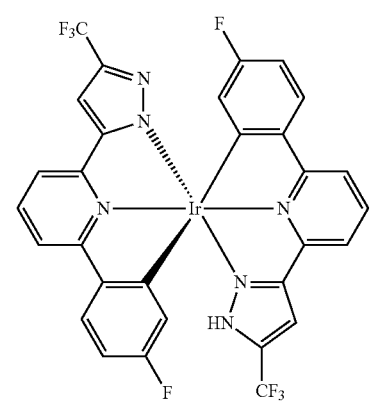
I-9
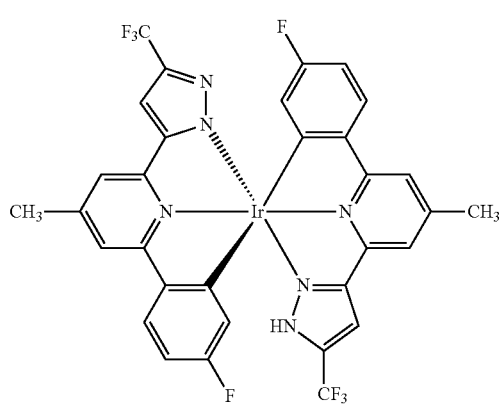
I-10
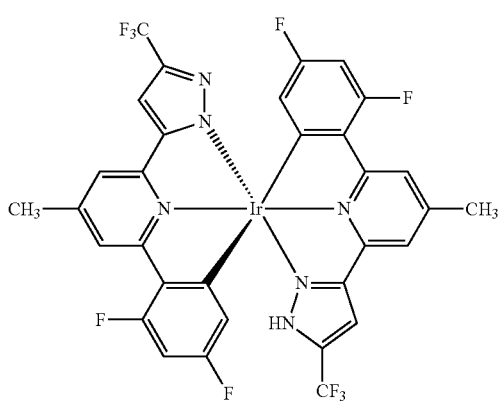
-continued
I-11
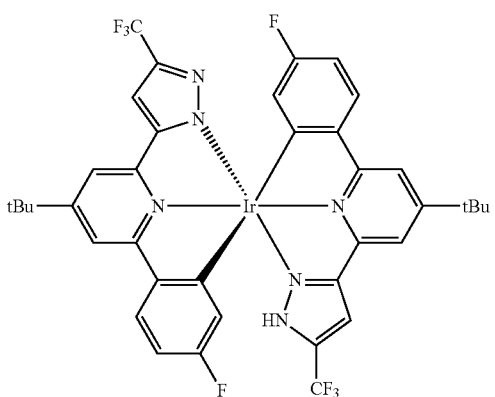
I-12
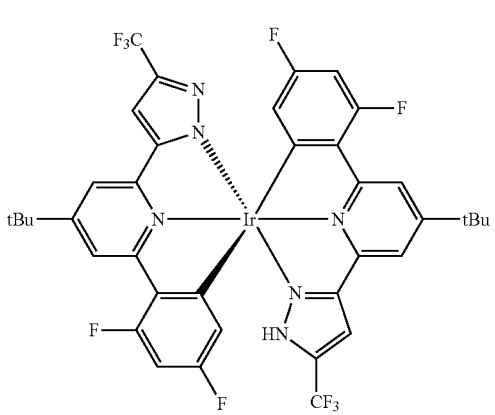
I-13
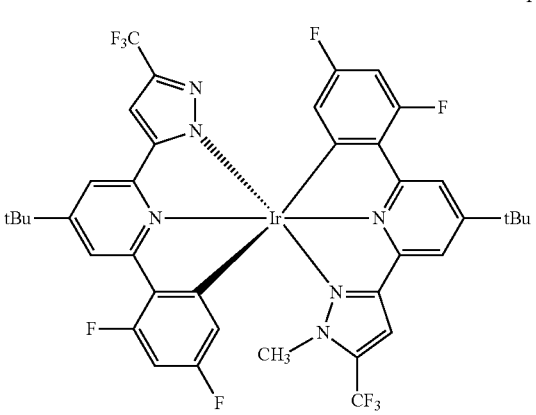
I-14
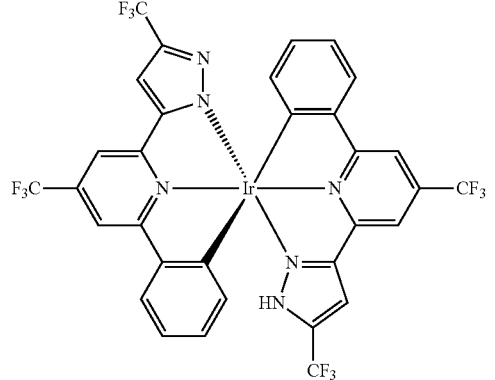

-continued
I-15
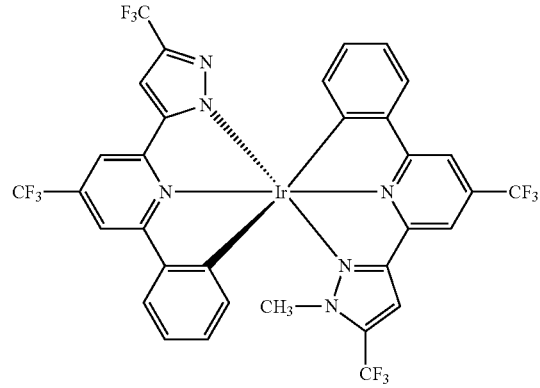
I-19
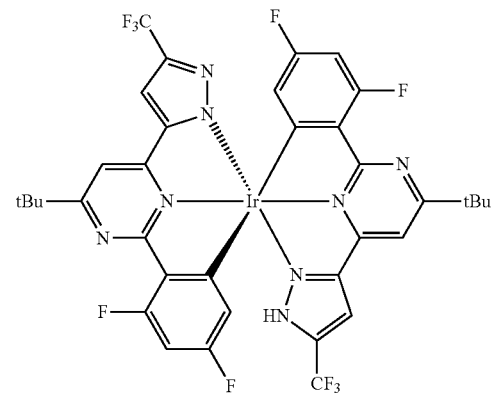
I-16
I-20
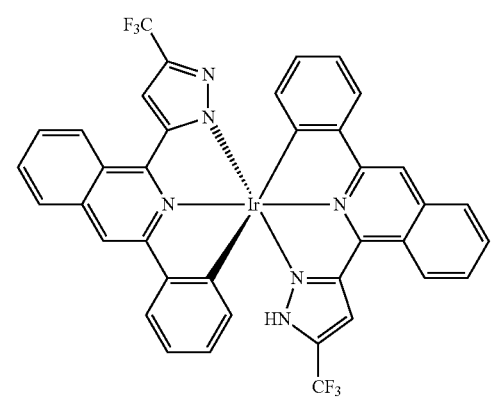
I-17
I-21
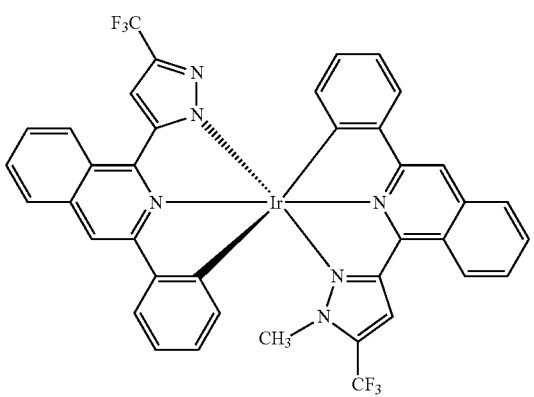
I-18
I-22
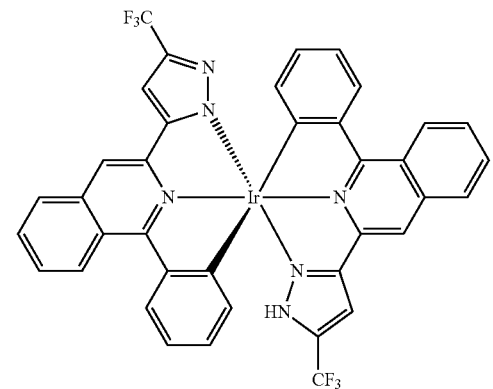

-continued
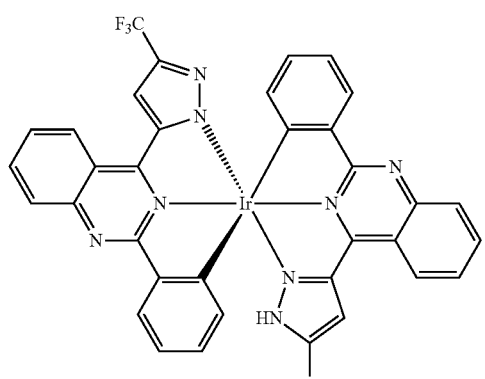
I-23
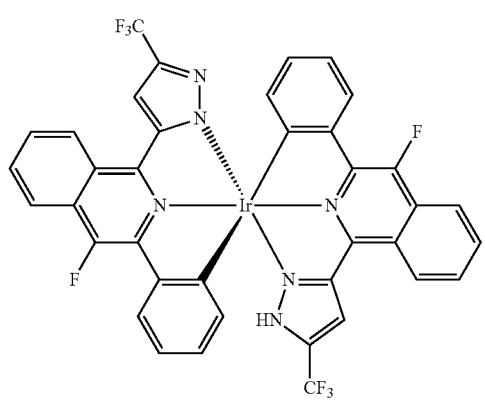
I-24
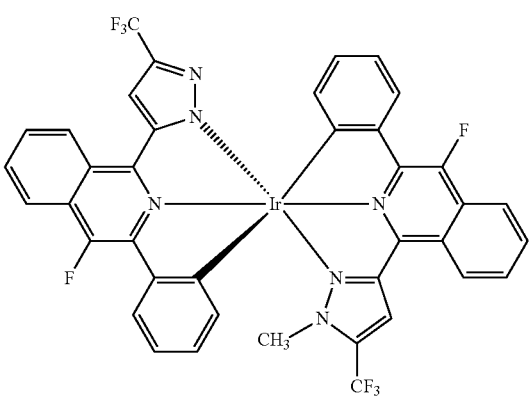
I-25
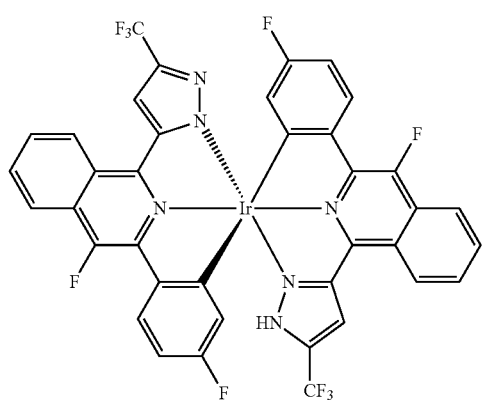
I-26
-continued
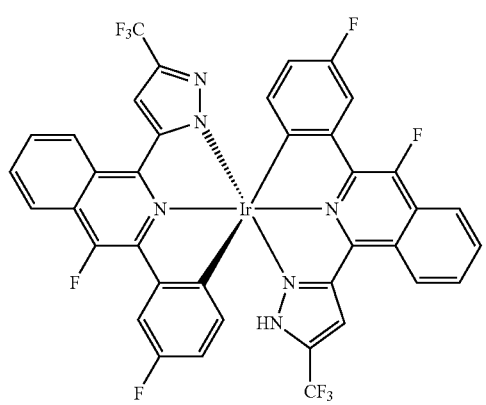
I-27
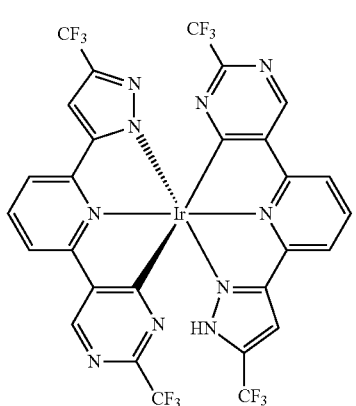
I-28
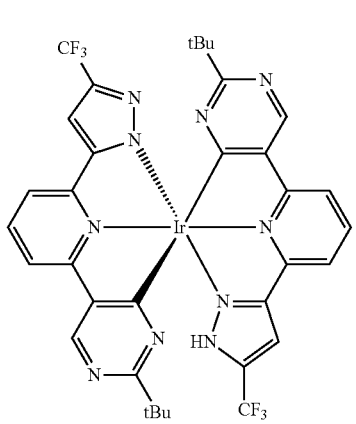
I-29
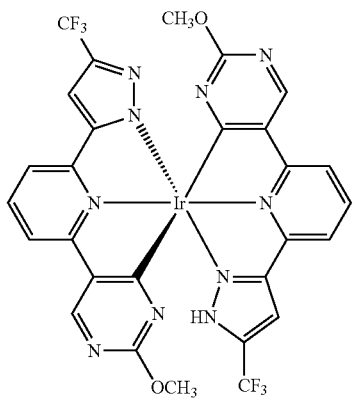
I-30

-continued
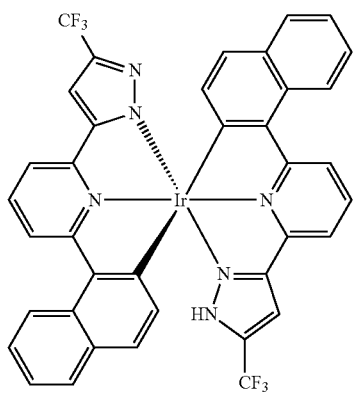
I-31
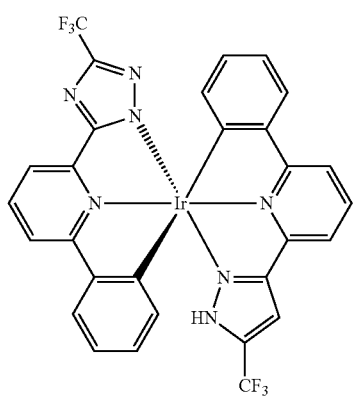
I-32
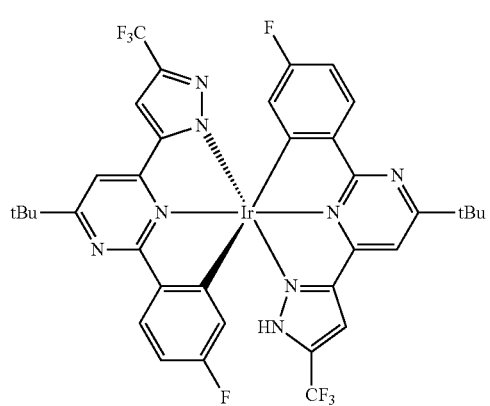
I-32-a
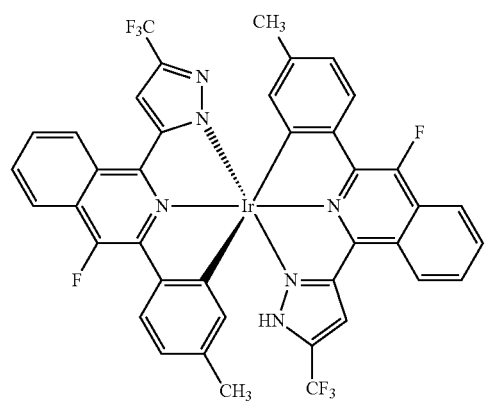
I-32-b
In another embodiment, the iridium complex is negatively charged. More specifically, in general formula (I), p and p' are 0, and the structure thereof can be represented by any one of formula (I-33) to formula (I-42) below:
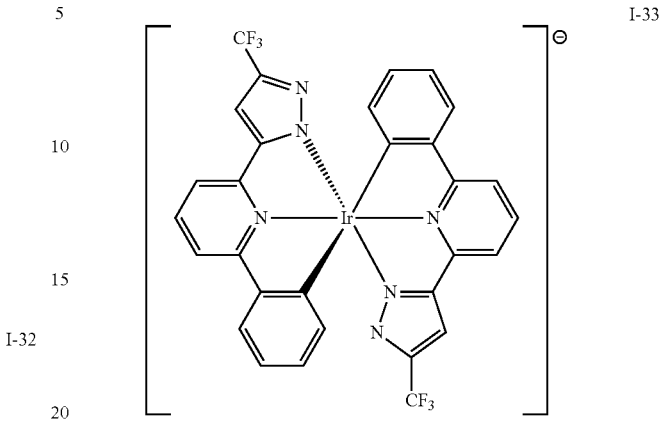
I-33
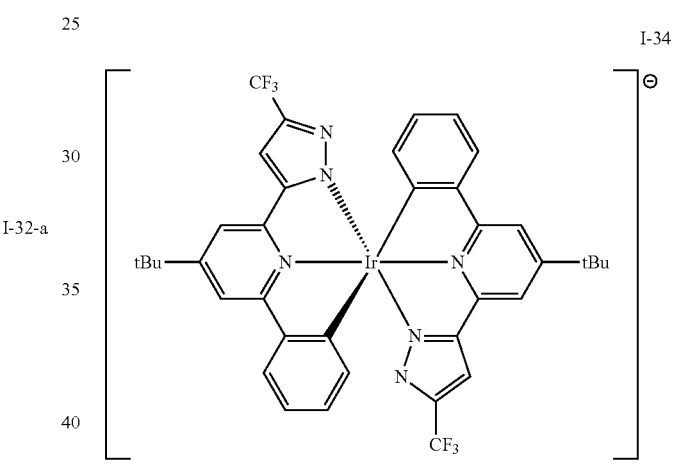
I-34
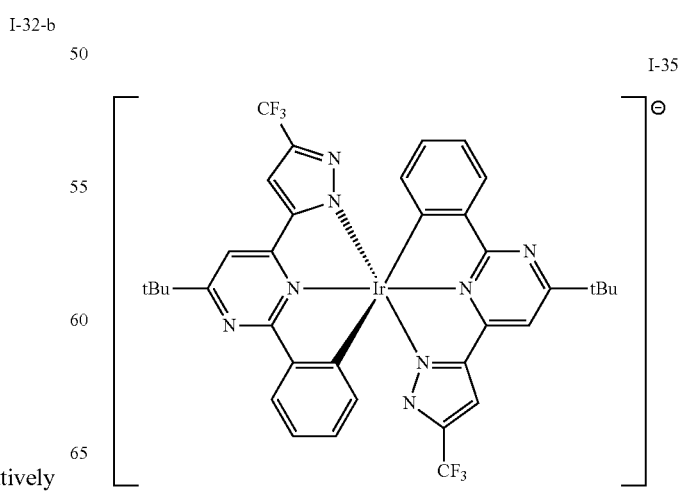
I-35

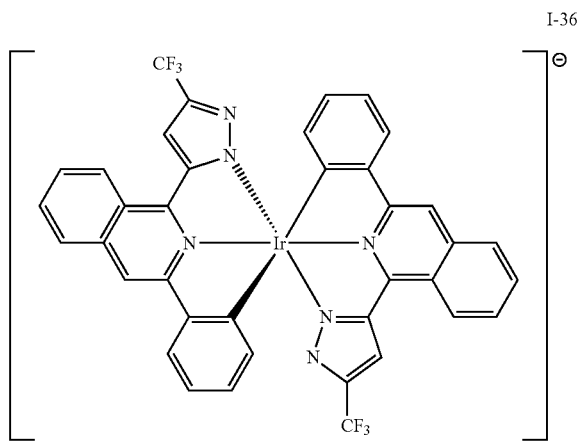
I-36
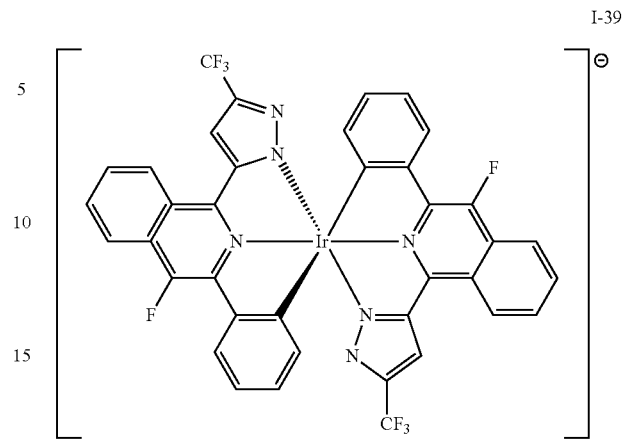
I-39
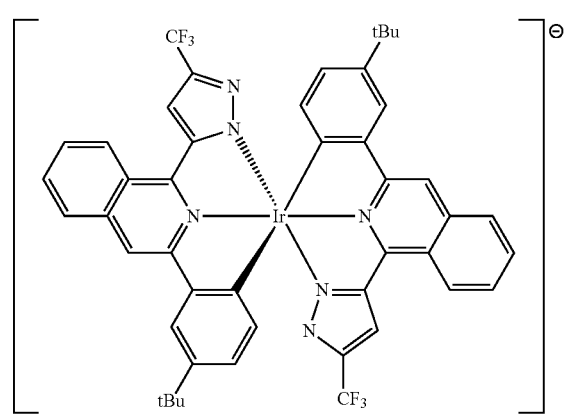
I-37
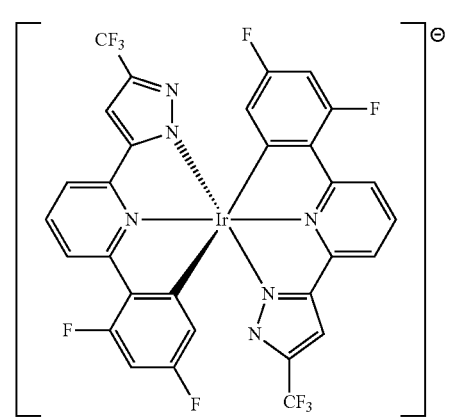
I-40
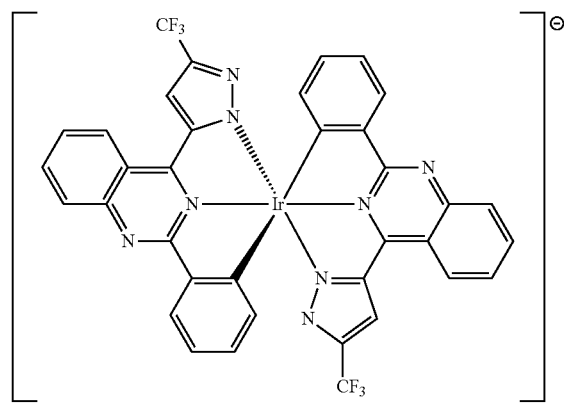
I-38
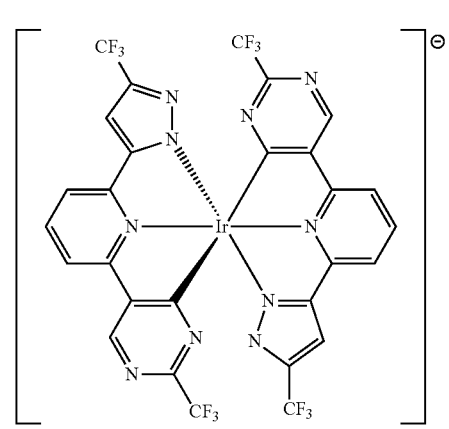
I-41

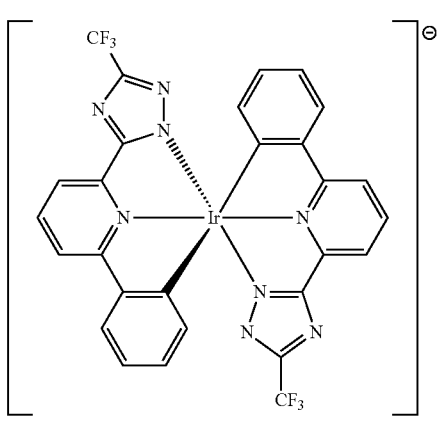
I-42
In yet another embodiment, the iridium complex is positively charged. More specifically, in general formula (I), p and p' are 1, and the structure thereof can be represented by any of formula (I-43) to formula (I-56) below:
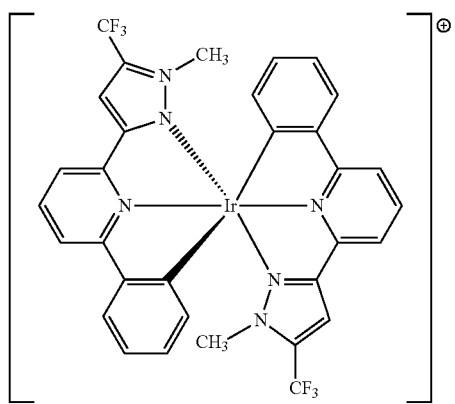
I-43
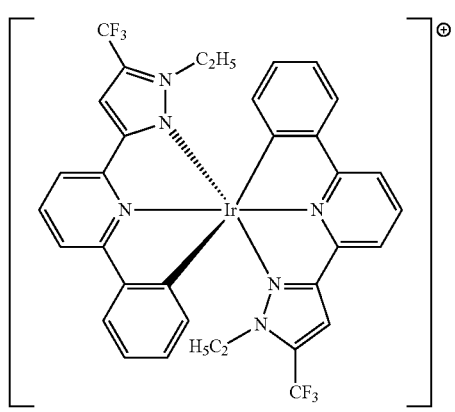
I-44
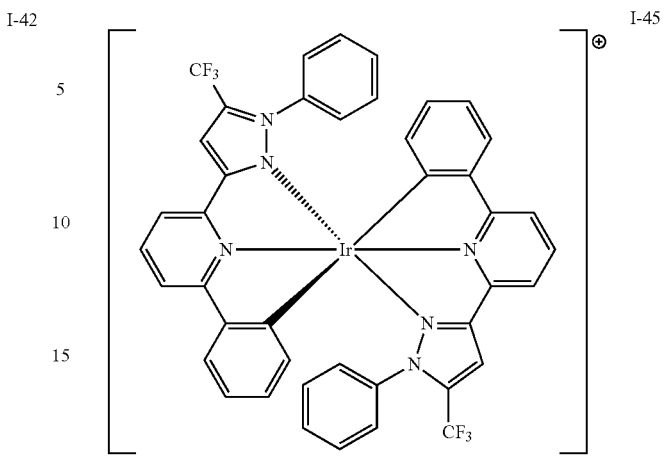
I-45
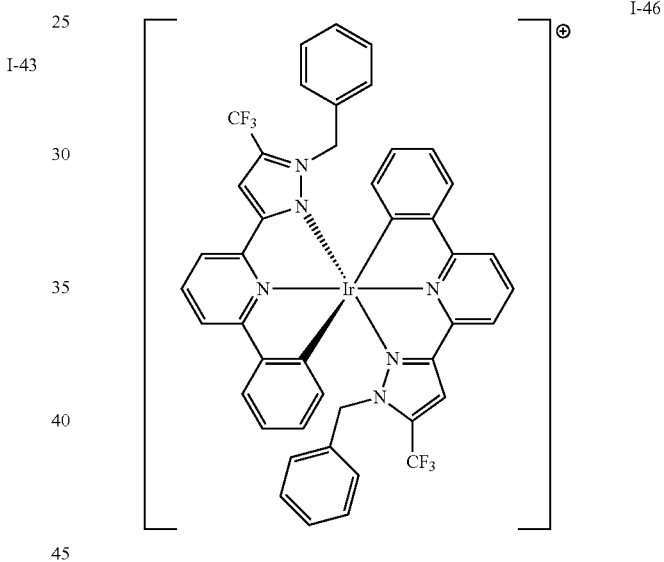
I-46
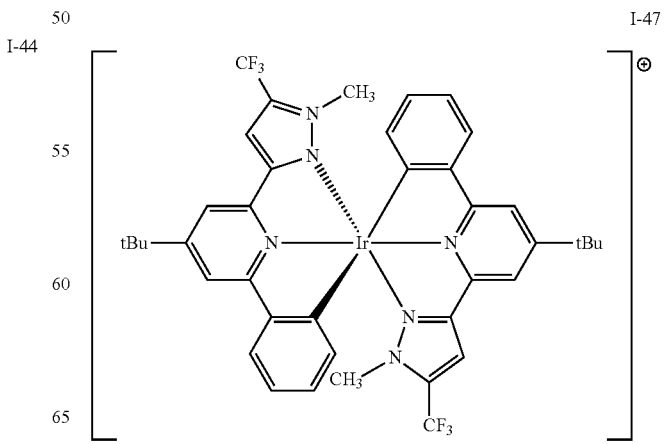
I-47

-continued
I-48
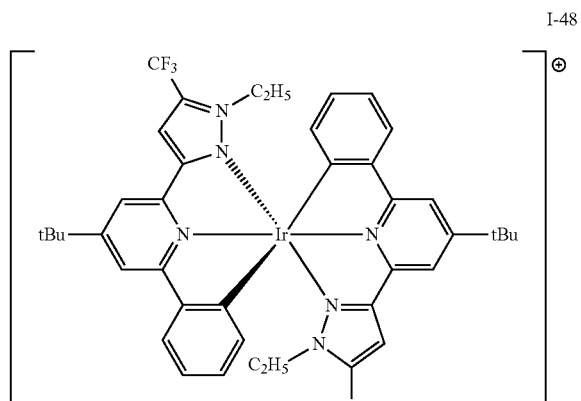
I-49
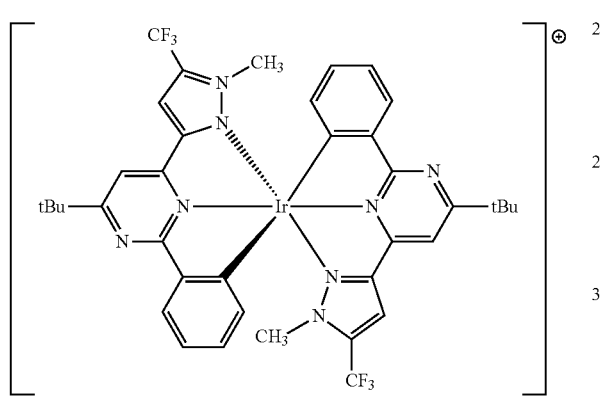
I-50
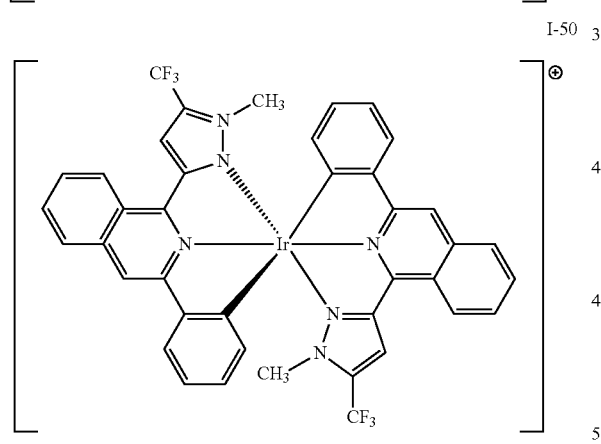
I-51
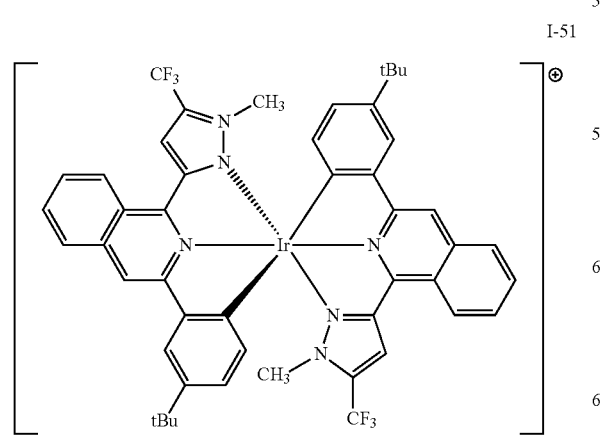
-continued
I-52
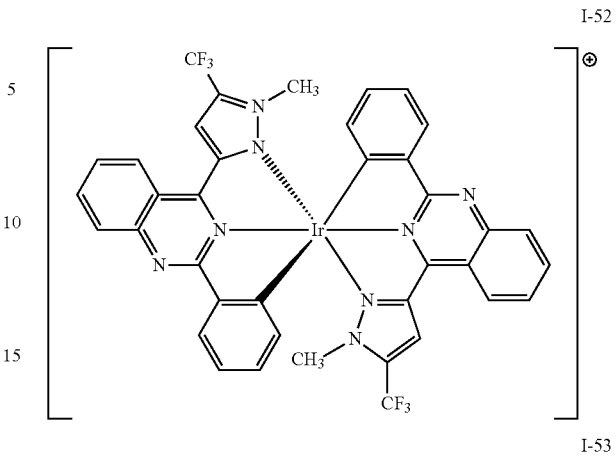
I-53
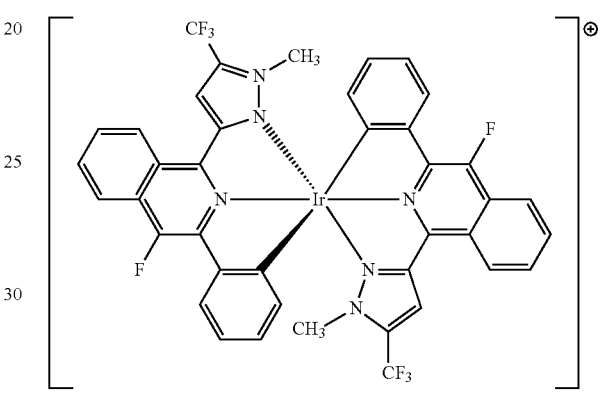
I-54
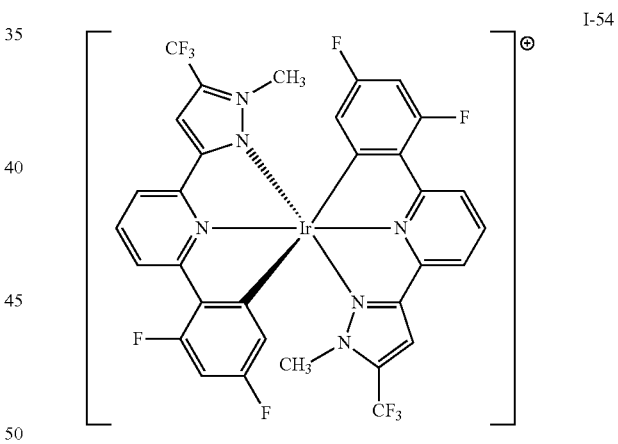
I-55
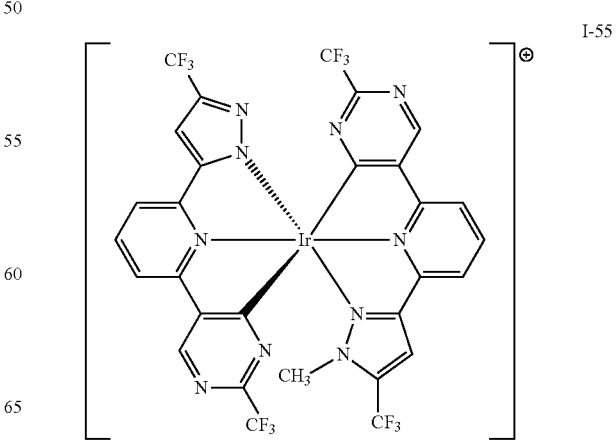

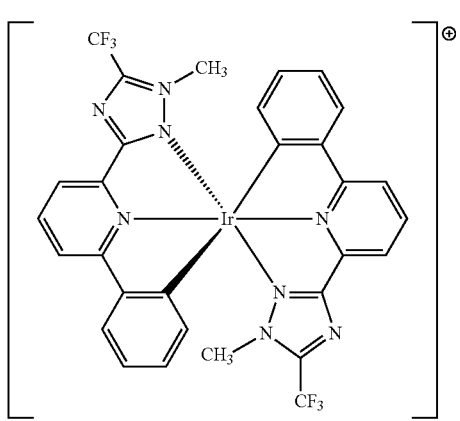
I-56
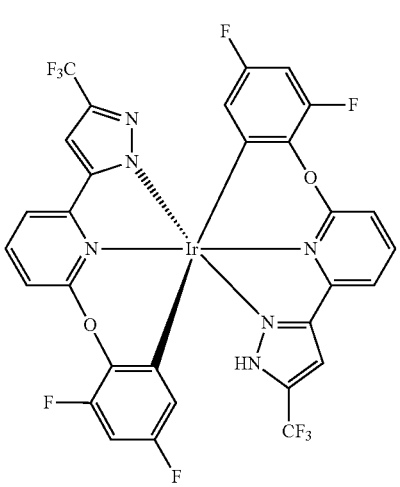
I-59
In an embodiment, a is 1, and the two ligands on the iridium complex respectively have a broken or interrupted conjugate structure.
In an embodiment, a is 1 and one of p and p' is 1, the other of p and p' is 0, the iridium complex is electrically neutral, and the structure thereof can be represented by any one of formula (I-57) to formula (I-64) below:
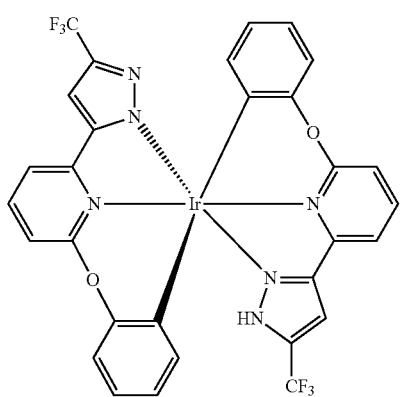
I-57
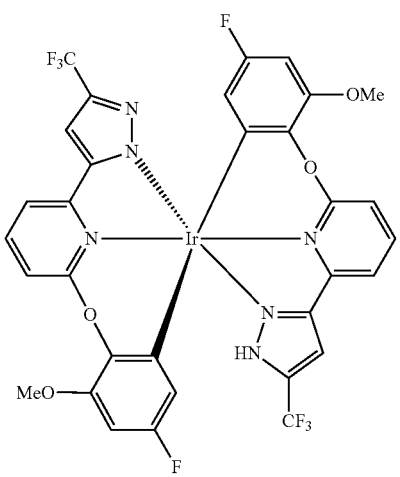
I-60
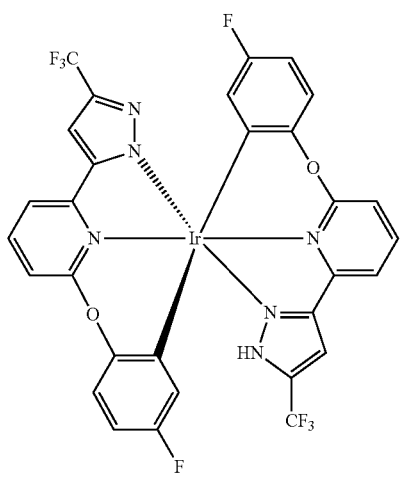
I-58
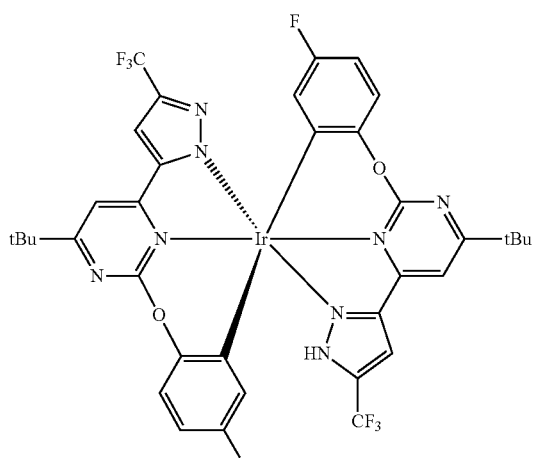
I-61

-continued

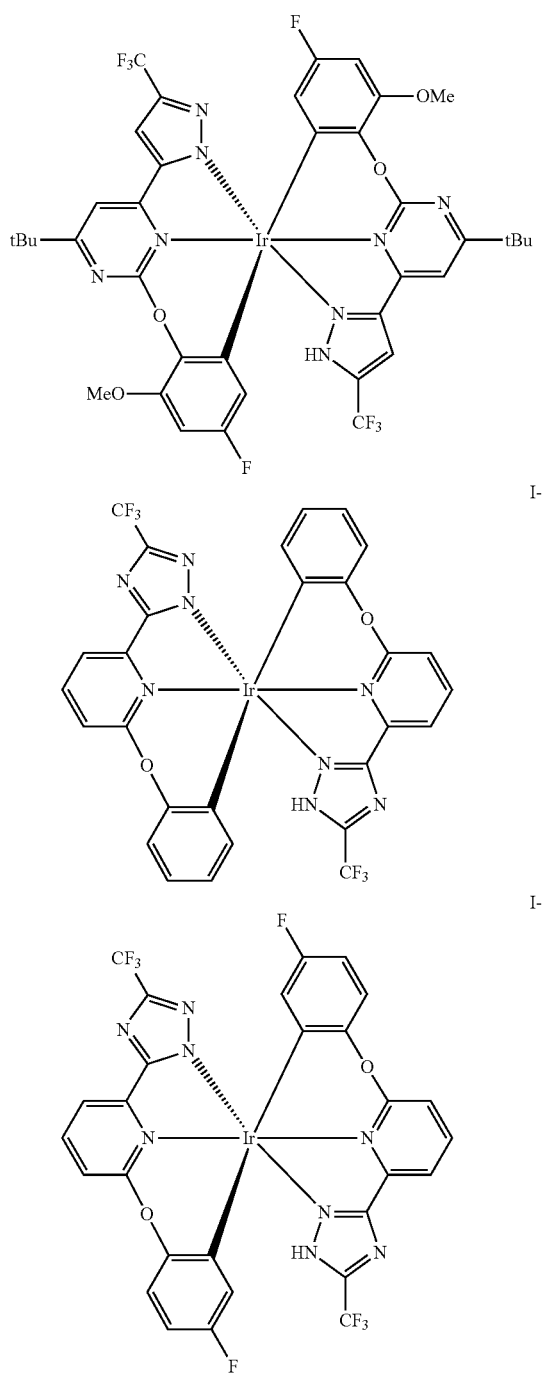

The bis-tridentate iridium complex of the invention has strong rigidity, high stability, and high luminous efficiency. Moreover, the structure of the iridium complex of the invention can also be modified via a simple reaction to change the valence state and formal charge on complex thereof, so as to expand the application thereof.

[Forming Method of Iridium Complex]

Forming Method of Electrically Neutral Iridium Complex

In an embodiment, the electrically neutral iridium complex of the invention can be obtained by the following reaction:

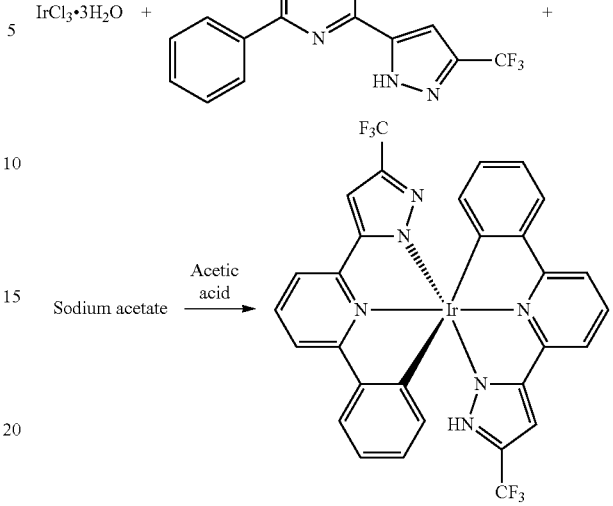

The electrically neutral iridium complex of the invention can be prepared by adopting suitable reactants and reaction conditions according to changes of each ligand, and the preparation method can be modified based on a known technique in the art. A specific example of the preparation method of the iridium complex of the invention contains the following steps: a precursor of the nitrogen-containing tridentate ligand of general formula (II) of the invention, an iridium metal precursor, and other required reagents are mixed and then heated to react.

In an embodiment, the structure of the ligand of the electrically charge-neutral iridium complex of the invention can be further modified via the following reaction:

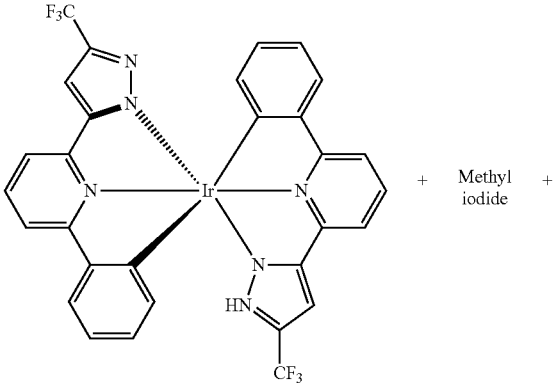

-continued

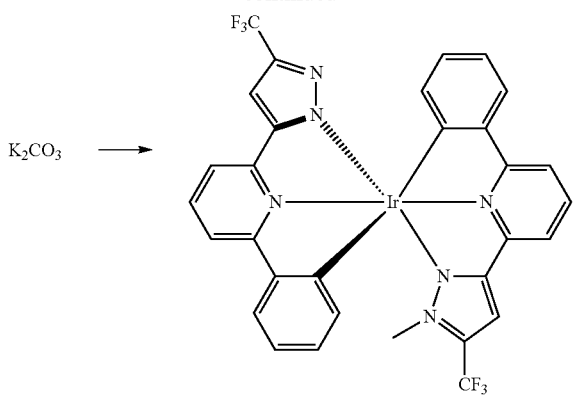

K₂CO₃ →

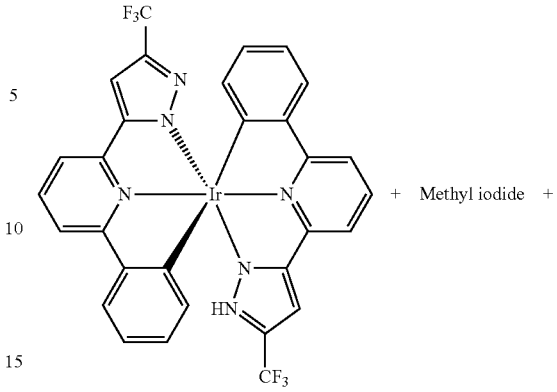

+ Methyl iodide +

In the invention, the electrically neutral iridium complex can be further modified by bonding a substituent to the ligand thereof, and thus, electrically charge-neutral iridium complexes having different structures can be obtained.

Forming Method of Negatively Charged Iridium Complex

The negatively charged iridium complex of the invention can be obtained by the following reaction:

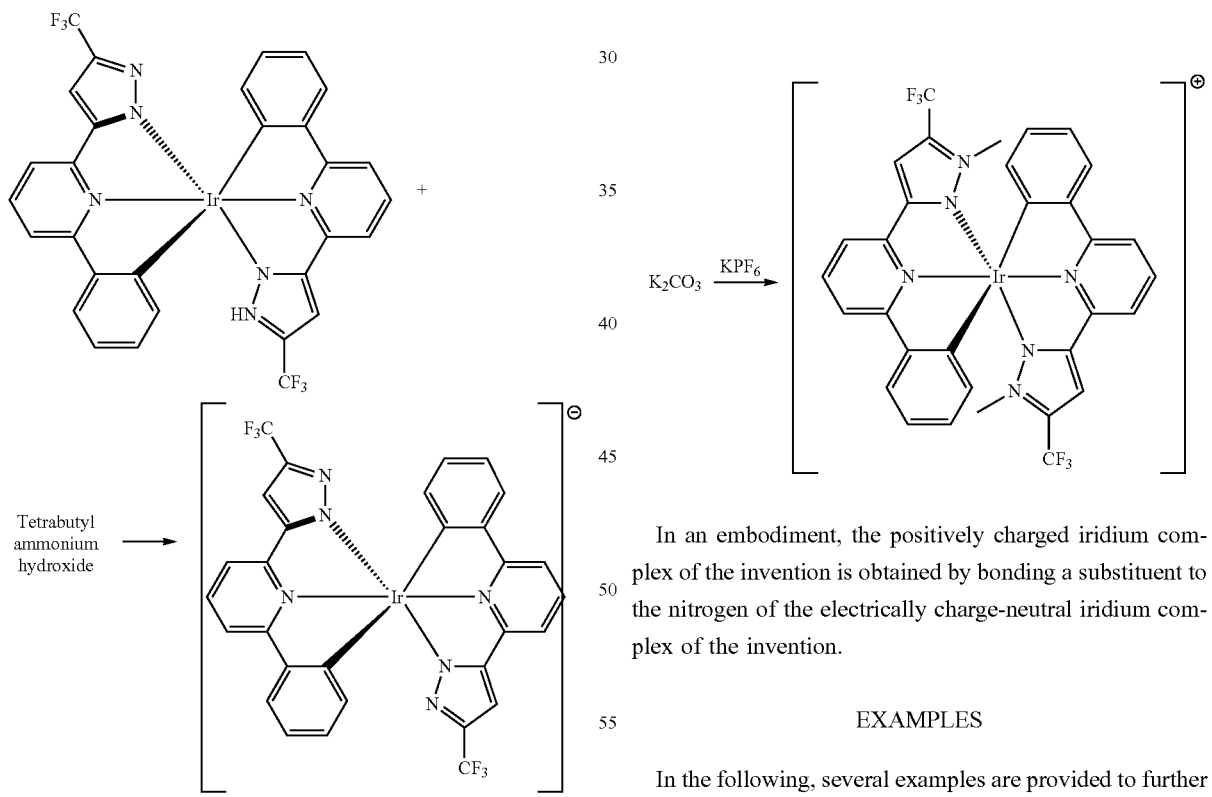

In an embodiment, the negatively charged iridium complex of the invention is obtained by further removing a proton from the electrically neutral iridium complex of the invention.

Forming Method of Positively Charged Iridium Complex

The positively charged iridium complex of the invention can be obtained by the following reaction:

In an embodiment, the positively charged iridium complex of the invention is obtained by bonding a substituent to the nitrogen of the electrically charge-neutral iridium complex of the invention.

EXAMPLES

In the following, several examples are provided to further describe the invention, but the examples are only exemplary and are not intended to limit the scope of the invention. The iridium complexes represented by formulas (I-1), (I-2), (I-3), (I-4), (I-5) . . . (I-64) are abbreviated as compounds (I-1), (I-2), (I-3), (I-4), (I-5) . . . (I-64) hereinafter. The abbreviations also apply to iridium complexes represented by other chemical structures in the following.

Example 1

Preparation of Compound (I-1):

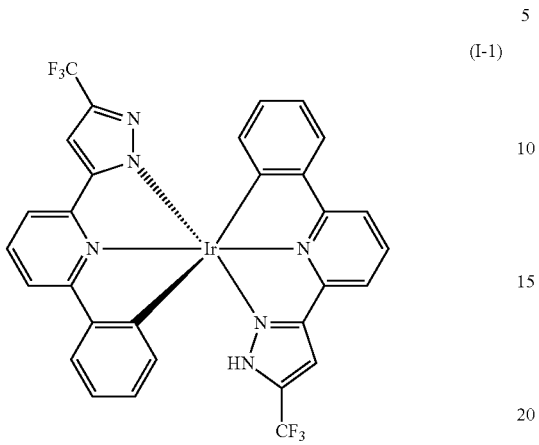

(I-1)

IrCl$_3$·3H$_2$O (100 mg, 0.28 mmol), 2-(5-trifluoromethyl-1H-pyrazol-3-yl)-6-phenylpyridine (164 mg, 0.57 mmol), and sodium acetate (465 mg, 5.67 mmol) were dissolved in acetic acid (20 mL) at room temperature and reacted at 110° C. for 24 hours. After the reaction was complete, the mixture was cooled to room temperature, and after acetic acid was removed via vacuum, washing was performed 3 times using water and ethyl acetate. A product was obtained after purification by column chromatography (ethyl acetate:hexane=1:4), with a yield of 78%.

Spectral data of compound (I-1): $^1$H NMR (400 MHz, CD$_2$Cl$_2$): δ 7.83 to 7.80 (br, 4H), 7.72 (s, 2H), 7.57 (s, 2H), 7.00 (s, 2H), 6.84 (s, 2H), 6.69 to 6.67 (br, 2H), 5.88 (s, 1H); $^{19}$F NMR (376 MHz, CD$_2$Cl$_2$): δ −60.71 (s, 6F); MS [FAB]: m/z 768.1, M$^+$.

FIG. 1 is a single crystal X-ray diffraction pattern of compound (I-1). It can be seen in FIG. 1 that proton transfer occurs to the precursor of the first ligand of compound (I-1), so that a negative monoanionic ligand is formed. Therefore, the nitrogen-containing five-membered heterocyclic ring on the first ligand of compound (I-1) has retained a proton (labeled as "H3"), which forms a hydrogen bond with an oxygen (labeled as "O1") on the ethyl acetate solvent. It can be further seen in FIG. 1 that proton transfer does not occur to the precursor of the second ligand of compound (I-1), so a dianionic ligand is formed. Therefore, the nitrogen-containing five-membered heterocyclic ring on the second ligand of compound (I-1) does not have an unremoved proton, so a hydrogen bond is not observed.

Example 2

Preparation of Compound (I-2):

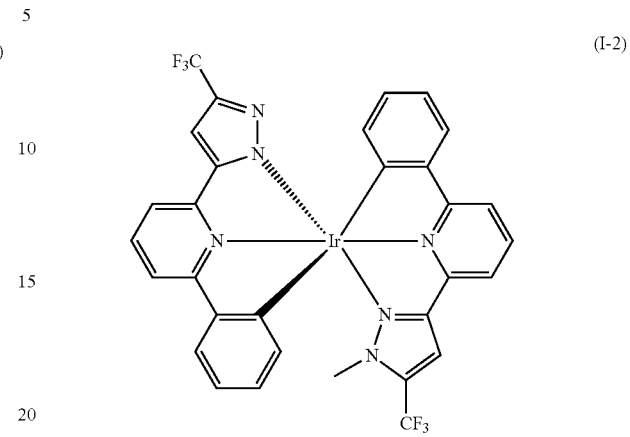

(I-2)

Compound (I-1) (100 mg, 0.13 mmol) was dissolved in tetrahydrofuran (10 mL), and then potassium carbonate (180 mg, 1.3 mmol) was added at room temperature. After stirring for 15 minutes, methyl iodide (184 mg, 1.3 mmol) was added to react for 2 hours. Then, washing was performed 3 times using water and ethyl acetate, and a product was obtained after purification by column chromatography (ethyl acetate:hexane=1:4), with a yield of 80%.

Spectral data of compound (I-2): $^1$H NMR (400 MHz, CDCl$_3$): δ 7.82 (d, J=8.0 Hz, 1H), 7.75 (t, J=8.0 Hz, 2H), 7.68 (d, J=7.6 Hz, 1H), 7.64 (d, J=8.0 Hz, 1H), 7.58 to 7.49 (m, 3H), 7.09 (s, 1H), 6.88 (s, 1H), 6.85 to 6.78 (m, 2H), 6.69 (t, J=7.4 Hz, 2H), 5.97 (d, J=7.6 Hz, 1H), 5.91 (d, J=7.4 Hz, 1H), 3.23 (s, 3H); $^{19}$F NMR (376 MHz, CDCl$_3$): δ −59.93 (s, 3F), −60.86 (s, 3F); MS [FAB]: m/z 782.1, M$^+$. Anal. Calcd for C$_{31}$H$_{19}$F$_6$IrN$_6$: C, 47.63; H, 2.45; N, 10.75. Found: C, 47.70; H, 2.66; N, 10.80.

Example 3

Preparation of Compound (I-7):

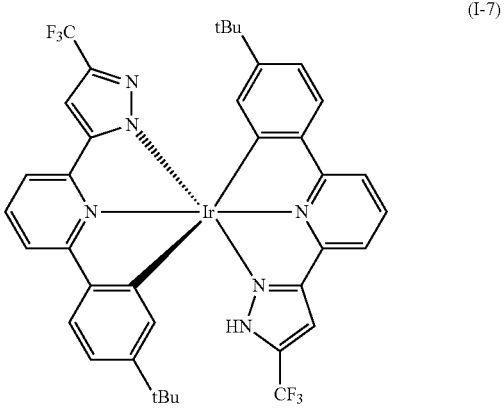

(I-7)

The synthesis steps of compound (I-7) were similar to those of compound (I-1), except that 2-(5-trifluoromethyl-1H-pyrazol-3-yl)-6-phenylpyridine was replaced by 2-(5-trifluoromethyl-1H-pyrazol-3-yl)-6-(4-tert-butylphenyl) pyridine. A product was then obtained, with a yield of 62%.

Spectral data of compound (I-7): $^1$H NMR (400 MHz, CD$_2$Cl$_2$): δ 7.8 (br, 2H), 7.69 (br, 6H), 7.41 (br, 2H), 6.85 (br, 4H), 0.91 (s, 18H); $^{19}$F NMR (376 MHz, CD$_2$Cl$_2$): δ −60.84 (br, 6F); MS [FAB]: m/z 879.2, M$^+$.

Example 4

Preparation of Compound (I-12):

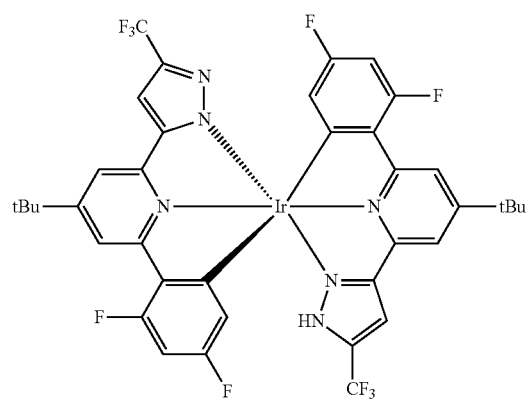

(I-12)

The synthesis steps of compound (I-12) were similar to those of compound (I-1), except that 2-(5-trifluoromethyl-1H-pyrazol-3-yl)-6-phenylpyridine was replaced by 2-(5-trifluoromethyl-1H-pyrazol-3-yl)-4-tert-butyl-6-(2,4-difluorophenyl)pyridine. A product was then obtained, with a yield of 62%.

Spectral data of compound (I-12): $^1$H NMR (400 MHz, CDCl$_3$): δ 8.10 (s, 2H), 7.69 (s, 2H), 6.91 (s, 2H), 6.29 (t, J=7.2 Hz, 2H), 5.19 (s, 2H), 1.24 (s, 18H); $^{19}$F NMR (376 MHz, CDCl$_3$): δ −60.39 (s, 6F), −107.03 to 110.47 (m, 4F); MS [FAB]: m/z 952.2, M$^+$.

Example 5

Preparation of Compound (I-13):

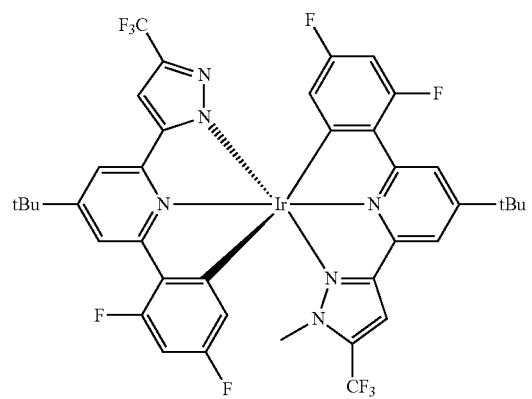

(I-13)

The synthesis steps of compound (I-13) were similar to those of compound (I-2), except that the initiator compound (I-1) was replaced by compound (I-12). A product was then obtained, with a yield of 73%.

Spectral data of compound (I-13): $^1$H NMR (400 MHz, CDCl$_3$): δ 8.20 (s, 1H), 8.01 (s, 1H), 7.70 (d, J=1.6 Hz, 1H), 7.60 (d, J=1.6 Hz, 1H), 7.15 (s, 1H), 6.91 (s, 1H), 6.37 to 6.29 (m, 1H), 5.38 (dd, J=8.2, 2.4 Hz, 1H), 5.32 (dd, J=8.2, 2.4 Hz, 1H), 3.22 (s, 3H), 1.51 (s, 9H), 1.52 (s, 9H); $^{19}$F NMR (376 MHz, CDCl$_3$): δ −60.03 (s, 3F), −60.92 (s, 3F), −106.44 to −106.52 (m, 1F), −107.28 to −107.35 (m, 1F), −110.22 to −110.28 (m, 1F), −110.37 to −110.43 (m, 1F); MS [FAB]: m/z 966.2, M$^+$. Anal. Calcd for C$_{39}$H$_{31}$F$_{10}$IrN$_6$: C, 48.50; H, 3.23; N, 8.70. Found: C, 48.75; H, 3.60; N, 8.71.

Example 6

Preparation of Compound (I-16):

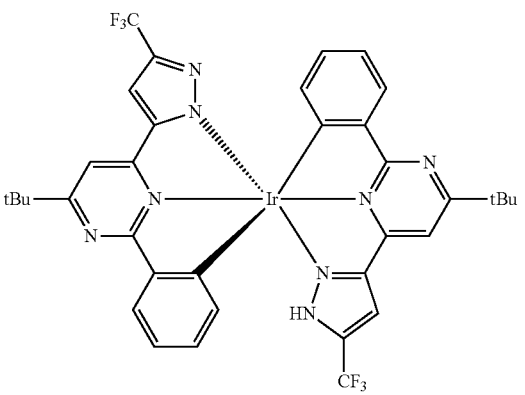

(I-16)

The synthesis steps of compound (I-16) were similar to those of compound (I-1), except that 2-(5-trifluoromethyl-1H-pyrazol-3-yl)-6-phenylpyridine was replaced by 2-(5-trifluoromethyl-1H-pyrazol-3-yl)-4-tert-butyl-6-phenylpyrimidine. A product was then obtained, with a yield of 48%.

Spectral data of compound (I-16): $^1$H NMR (400 MHz, CDCl$_3$): δ 7.90 (d, J=7.4 Hz, 2H), 7.56 (s, 2H), 6.91 (br, 2H), 6.78 (t, J=7.4 Hz, 2H), 6.64 (t, J=7.4 Hz, 2H), 5.45 (br, 2H) 1.61 (s, 18H); $^{19}$F NMR (376 MHz, CD$_2$Cl$_2$): δ −60.63 (br, 6F); MS [FAB]: m/z 882.2, M$^+$.

Example 7

Preparation of Compound (I-17):

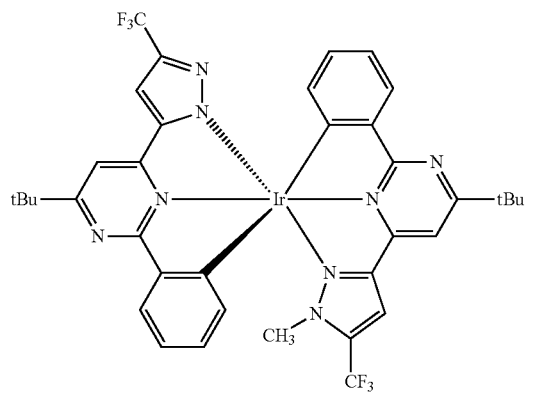

(I-17)

Compound (I-16) (100 mg, 0.13 mmol) was dissolved in tetrahydrofuran (10 mL), and then potassium carbonate (180 mg, 1.3 mmol) was added at room temperature. After stirring for 15 minutes, methyl iodide (184 mg, 1.3 mmol) was added to react for 1.5 hours. Then, washing was performed 3 times using water and ethyl acetate, and a product was obtained after purification by column chromatography (ethyl acetate:hexane=1:1), with a yield of 80%.

Spectral data of compound (I-17): $^1$H NMR (400 MHz, CDCl$_3$): δ 8.03 (dd, J=7.7, 1.4 Hz, 1H), 8.00 (dd, J=7.7, 1.4 Hz, 1H), 7.68 (s, 1H), 7.52 (s, 1H), 7.30 (s, 1H), 7.08 (s, 1H), 6.92 (td, J=7.4, 1.1 Hz, 1H), 6.89 (td, J=7.4, 1.1 Hz 1H), 6.80 (dt, J=7.4, 1.3 Hz, 1H), 6.79 (dt, J=7.4, 1.3 Hz, 1H), 5.94 (dd, J=7.4, 0.6 Hz, 1H), 5.86 (dd, J=7.4, 0.6 Hz, 1H) 3.28 (s, 3H), 1.61 (s, 9H), 1.59 (s, 9H); $^{19}$F NMR (376 MHz, CDCl$_3$): δ −60.17 (s, 3F), −60.91 (s, 3F).

Example 8

Preparation of Compound (I-18):

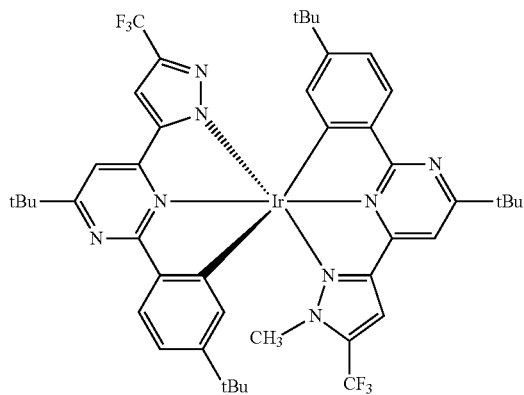

(I-18)

The synthesis steps of compound (I-18) were similar to those of compound (I-1), except that 2-(5-trifluoromethyl-1H-pyrazol-3-yl)-6-phenylpyridine was replaced by 2-(5-trifluoromethyl-1H-pyrazol-3-yl)-4-tert-butyl-6-(4-tert-butylphenyl)pyrimidine. A product was then obtained, with a yield of 56%. The above compound (100 mg, 0.13 mmol) was dissolved in tetrahydrofuran (10 mL), and then potassium carbonate (180 mg, 1.3 mmol) was added at room temperature. After stirring for 15 minutes, methyl iodide (184 mg, 1.3 mmol) was added to react for 1.5 hours. Then, washing was performed 3 times using water and ethyl acetate, and a final product was obtained after purification by column chromatography (ethyl acetate:hexane=1:1), with a yield of 81%.

Spectral data of compound (I-18): $^1$H NMR (400 MHz, CDCl$_3$): δ 7.88 (d, J=8.1 Hz, 1H), 7.84 (d, J=8.1 Hz, 1H), 7.68 (s, 1H), 7.52 (s, 1H), 7.31 (s, 1H), 7.09 (s, 1H), 6.92 (dd, J=8.2, 1.9 Hz, 1H), 6.89 (dd, J=8.1, 1.9 Hz, 1H), 5.80 (d, J=1.8 Hz, 1H), 5.71 (d, J=1.8 Hz, 1H), 3.28 (s, 3H), 1.58 (s, 9H), 1.57 (s, 9H), 0.97 (s, 9H), 0.96 (s, 9H); $^{19}$F NMR (376 MHz, CD$_2$Cl$_2$): δ −60.13 (s, 3F), −60.94 (s, 3F).

Example 9

Preparation of Compound (I-20):

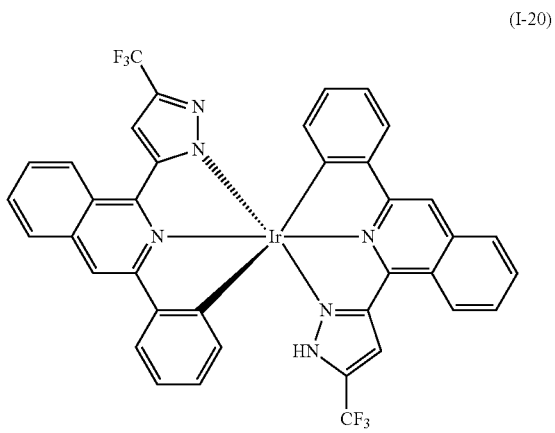

(I-20)

The synthesis steps of compound (I-20) were similar to those of compound (I-1), except that 2-(5-trifluoromethyl-1H-pyrazol-3-yl)-6-phenylpyridine was replaced by 1-(5-trifluoromethyl-1H-pyrazol-3-yl)-3-phenylisoquinoline. A product was then obtained, with a yield of 76%.

Spectral data of compound (I-20): $^1$H NMR (400 MHz, CDCl$_3$): δ 8.64 (s, 2H), 8.09 (s, 2H), 8.03 (s, 2H), 7.71 (s, 4H), 7.60 (d, J=7.4 Hz, 2H), 7.46 (s, 2H), 6.80 (t, J=7.2 Hz, 2H), 6.58 (t, J=7.4 Hz, 2H), 5.76 (d, J=7.2 Hz, 2H); $^{19}$F NMR (376 MHz, CDCl$_3$): δ −60.34 (s, 6F); MS [FAB]: m/z 868.1, M$^+$.

Example 10

Preparation of Compound (I-21):

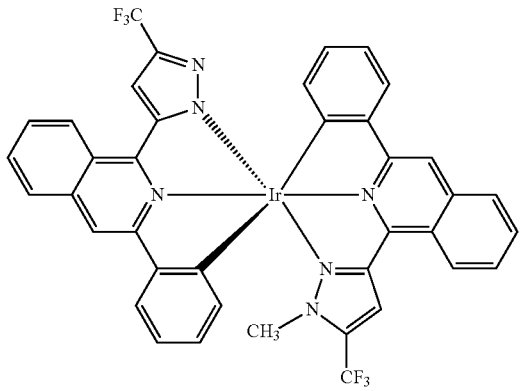

(I-21)

The synthesis steps of compound (I-21) were similar to those of compound (I-2), except that the initiator compound (I-1) was replaced by compound (I-20). A product was then obtained, with a yield of 80%.

Spectral data of compound (I-21): $^1$H NMR (400 MHz, CD$_2$Cl$_2$): δ 8.72 (m, 1H), 8.54 (d, J=8 Hz, 1H), 8.11 (s, 1H), 8.05 (m, 2H), 7.95 (d, J=7.6 Hz, 1H), 7.76 to 7.71 (m, 3H), 7.68 (t, J=11.6 Hz, 2H), 7.61 to 7.55 (m, 2H), 7.40 (s, 1H), 6.84 (t, J=6.2 Hz, 1H), 6.81 (t, J=6.2 Hz, 1H), 6.63 (q, J=7.8 Hz, 2H), 5.83 (d, J=7.6 Hz, 1H), 5.75 (d, J=7.2 Hz, 1H), 3.18

(s, 3H); $^{19}$F NMR (376 MHz, CDCl$_3$): δ −60.48 (s, 3F), −61.12 (s, 3F); MS [FAB]: m/z 882.2, M$^+$. Anal. Calcd for C$_{39}$H$_{23}$F$_6$IrN$_6$: C, 53.12; H, 2.63; N, 9.53. Found: C, 53.28; H, 2.98; N, 9.62.

Example 11

Preparation of Compound (I-23):

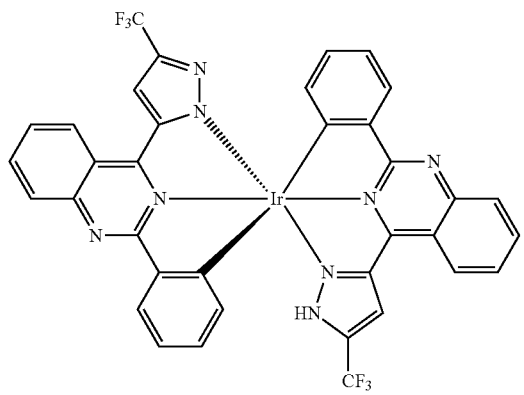

(I-23)

The synthesis steps of compound (I-23) were similar to those of compound (I-1), except that 2-(5-trifluoromethyl-1H-pyrazol-3-yl)-6-phenylpyridine was replaced by 2-phenyl-4-(5-trifluoromethyl-1H-pyrazol-3-yl)quinazoline. A product was than obtained, with a yield of 41%.

Spectral data of compound (I-23): $^1$H NMR (400 MHz, CDCl$_3$): δ 8.62 (s, 2H), 8.21 (s, 2H), 8.06 (s, 2H), 7.93 (s, 2H), 7.77 (s, 2H), 7.56 (s, 2H), 6.91 (s, 2H), 6.72 (s, 2H), 6.02 (s, 2H); $^{19}$F NMR (376 MHz, CDCl$_3$): δ −60.49 (s, 6F); MS [FAB]: m/z 870.1, M$^+$.

Example 12

Preparation of Compound (I-25):

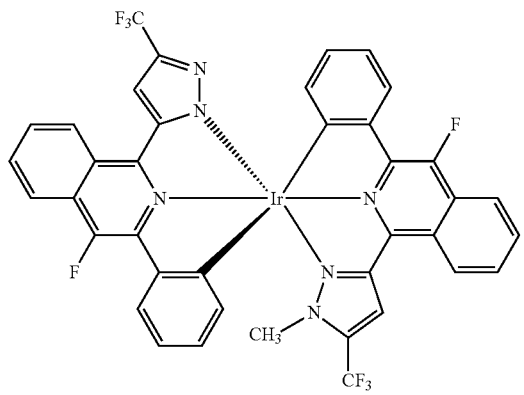

(I-25)

The synthesis steps of compound (I-25) were similar to those of compound (I-1), except that 2-(5-trifluoromethyl-1H-pyrazol-3-yl)-6-phenylpyridine was replaced by 1-(5-trifluoromethyl-1H-pyrazol-3-yl)-4-fluoro-3-phenylisoquinoline. A product was than obtained, with a yield of 52%. The above compound (100 mg, 0.13 mmol) was dissolved in tetrahydrofuran (10 mL), and then potassium carbonate (180 mg, 1.3 mmol) was added at room temperature. After stirring for 15 minutes, methyl iodide (184 mg, 1.3 mmol) was added and reacted for 2.5 hours. Then, washing was performed 3 times using water and ethyl acetate, and a final product was obtained after purification by column chromatography (ethyl acetate:hexane=2:3), with a yield of 70%.

Spectral data of compound (I-25): $^1$H NMR (400 MHz, CDCl$_3$): δ 8.78 (t, J=9.8 Hz, 2H), 8.38 (dd, J=7.5, 1.8 Hz, 1H), 8.19 (d, J=8.2 Hz, 1H), 8.08 (t, J=7.9 Hz, 2H), 7.86 (m, 3H), 7.73 (t, J=7.5 Hz, 1H), 7.56 (t, J=7.5 Hz, 1H), 7.41 (s, 1H), 9.62 (t, J=7.3 Hz, 1H), 6.89 (t, J=7.3 Hz, 1H), 6.69 (td, J=7.3, 1.0 Hz, 1H), 6.63 (td, J=7.3, 1.0 Hz, 1H), 5.86 (dd, J=7.6, 1.0 Hz, 1H), 5.75 (dd, J=7.6, 1.0 Hz, 1H), 3.21 (s, 3H); $^{19}$F NMR (376 MHz, CD$_2$Cl$_2$): δ −60.17 (s, 3F), −60.82 (s, 3F), δ −132.87 (s, 1F), −137.66 (s, 1F).

Example 13

Preparation of Compound (I-33):

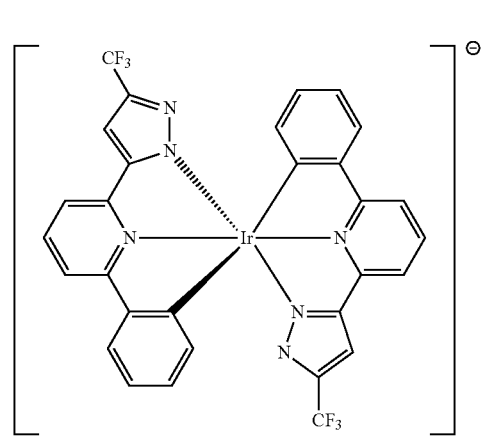

(I-33)

Compound (I-1) (100 mg, 0.13 mmol) was dissolved in methanol (10 mL), and then a 1.0 M tetrabutylammonium hydroxide solution was added at room temperature. After stirring for 30 minutes, a large amount of water was added to precipitate the mixture, solid was collected after suction and filtering, and then the product was purified by washing with water and a small amount of ether. The yield was 91%.

Spectral data of compound (I-33): $^1$H NMR (400 MHz, CD$_2$Cl$_2$): δ 7.71 to 7.64 (m, 4H), 7.56 to 7.54 (m, 4H), 6.87 (s, 2H), 6.79 (t, J=7.4 Hz, 2H), 6.64 (t, J=7.4 Hz, 2H), 6.04 (d, J=7.4 Hz, 2H), 2.74 to 2.70 (m, 8H), 1.34 to 1.27 (m, 8H), 1.21 to 1.15 (m, 8H), 0.88 (t, J=7.2 Hz, 12H); $^{19}$F NMR (376 MHz, CD$_2$Cl$_2$): δ −59.37 (s, 6F); MS [FAB]: m/z 767.2, [M$^+$-NBu$_4$]. Anal. Calcd for C$_{42}$H$_{52}$F$_6$IrN$_7$: C, 54.75; H, 5.19; N, 9.72. Found: C, 54.70; H, 5.35; N, 9.54.

Example 14

Preparation of Compound (I-35):

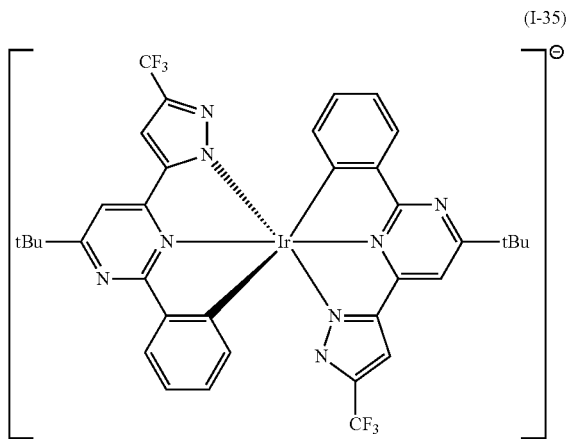

Compound (I-16) (100 mg, 0.13 mmol) was dissolved in methanol (10 mL), and then a 1.0 M tetrabutylammonium hydroxide solution was added at room temperature. After stirring for 30 minutes, a large amount of water was added to precipitate the mixture, solid was collected after suction and filtering, and then the product was purified by washing with water and a small amount of ether. The yield was 85%.

Spectral data of compound (I-35): $^1$H NMR (400 MHz, CD$_2$Cl$_2$): δ 7.94 (dd, J=7.5, 1.0 Hz, 2H), 7.44 (s, 2H), 6.99 (s, 2H), 6.76 (td, J=7.4, 1.1 Hz, 2H), 6.67 (td, J=7.4, 1.1 Hz, 2H), 5.94 (dd, J=7.5, 1.0 Hz, 2H), 1.59 (s, 18H); $^{19}$F NMR (376 MHz, CD$_2$Cl$_2$): δ −58.85 (s, 6F).

Example 15

Preparation of Compound (I-36):

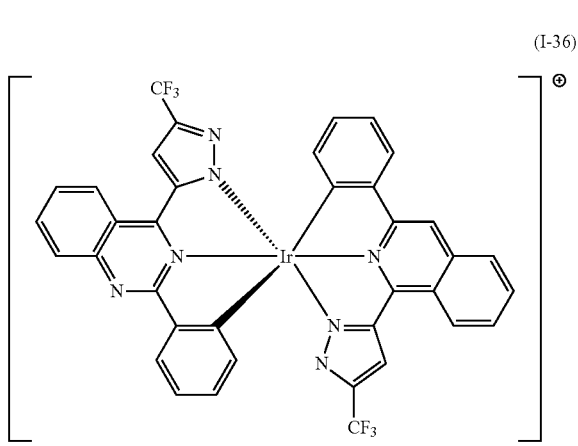

Compound (I-20) (100 mg, 0.13 mmol) was dissolved in methanol (10 mL), and then a 1.0 M tetrabutylammonium hydroxide solution was added at room temperature. After stirring for 30 minutes, a large amount of water was added to precipitate the mixture, solid was collected after suction and filtering, and then the product was purified by washing with water and a small amount of ether. The yield was 85%.

Spectral data of compound (I-36): $^1$H NMR (400 MHz, CD$_2$Cl$_2$): δ 8.87 (d, J=7.6 Hz, 2H), 8.27 (s, 2H), 8.17 (d, J=6 Hz, 2H), 7.76 to 7.70 (dt, J=6, 1.6 Hz, 4H), 7.69 (d, J=6.8 Hz, 2H), 7.46 (s, 2H), 6.68 to 6.64 (dt, J=7.6, 1.2 Hz, 2H), 6.47 to 6.43 (dt, J=7.2, 1.2 Hz, 2H), 6.00 to 5.98 (dd, J=7.6, 1.2 Hz, 2H), 3.35 (m, 8H), 1.77 to 1.68 (m, 8H), 1.40 to 1.29 (m, 8H), 0.94 (t, J=7.2 Hz, 12H); $^{19}$F NMR (376 MHz, CDCl$_3$): δ −59.78 (s, 6F).

Example 16

Preparation of Compound (I-43):

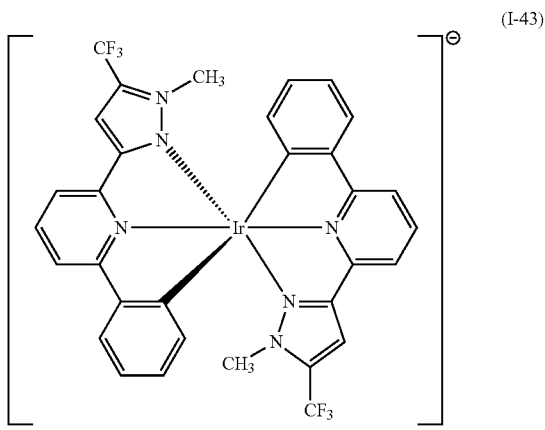

Compound (I-1) (100 mg, 0.13 mmol) was dissolved in tetrahydrofuran (10 mL), and then potassium carbonate (180 mg, 1.3 mmol) was added at room temperature. After stirring for 15 minutes, methyl iodide (184 mg, 1.3 mmol) was added. After reacting for 12 hours, the crude product was washed 3 times using water and ethyl acetate. The crude product was dissolved in methanol (10 mL), and an aqueous solution of ammonium hexafluorophosphate was added to perform ion exchange. After stirring for 1 hour, suction and filtering were performed to collect a solid. The product was purified by washing with water and a small amount of ether. The yield was 88%.

Spectral data of compound (I-43): $^1$H NMR (400 MHz, CD$_2$Cl$_2$): δ 8.07 to 7.99 (m, 4H), 7.95 (d, J=7.4 Hz, 2H), 7.65 (d, J=7.6 Hz, 2H), 7.35(s, 2H), 6.96 (t, J=7.4 Hz, 2H), 6.81 (t, J=7.4 Hz, 2H), 5.91 (d, J=7.6 Hz, 2H), 3.31 (s, 6H); $^{19}$F NMR (376 MHz, CD$_2$Cl$_2$): δ −61.33 (s, 6F, 2CF$_3$), −73.54 (d, J=710 Hz, 6F, PF$_6^-$); MS [FAB]: m/z 797.2, [M$^+$-PF$_6$].

Example 17

Preparation of Compound (I-49):

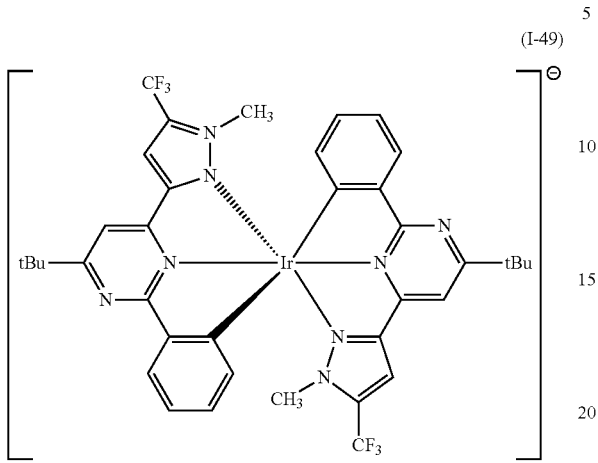

(I-49)

The synthesis steps of compound (I-49) were similar to those of compound (I-43), except that 2-(5-trifluoromethyl-1H-pyrazol-3-yl)-6-phenylpyridine was replaced by 2-(5-trifluoromethyl-1H-pyrazol-3-yl)-4-tert-butyl-6-phenylpyrimidine. A product was then obtained, with a yield of 82%.

Spectral data of compound (I-49): $^1$H NMR (400 MHz, CD$_2$Cl$_2$): δ 8.05 (dd, J=7.5, 1.2 Hz, 2H), 7.87 (s, 2H), 7.48 (s, 2H), 6.99 (td, J=7.5, 1.0 Hz, 2H), 6.87 (td, J=7.4, 1.2 Hz, 2H), 5.81 (dd, J=7.4, 1.0 Hz, 2H), 3.35 (s, 6H), 1.25 (s, 18H); $^{19}$F NMR (376 MHz, CD$_2$Cl$_2$): δ −60.9 (s, 6F, 2CF$_3$), −70.00 (d, J=712 Hz, 6F, PF$_6^-$).

Example 18

Preparation of Compound (I-50):

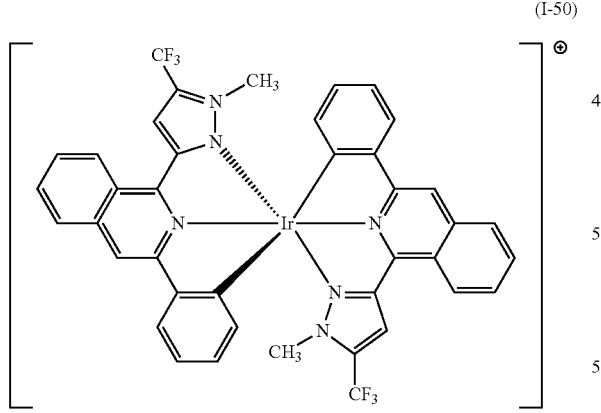

(I-50)

The synthesis steps of compound (I-50) were similar to those of compound (I-43), except that 2-(5-trifluoromethyl-1H-pyrazol-3-yl)-6-phenylpyridine was replaced by 1-(5-trifluoromethyl-1H-pyrazol-3-yl)-3-phenylisoquinoline. A product was then obtained, with a yield of 82%.

Spectral data of compound (I-50): $^1$H NMR (400 MHz, CD$_2$Cl$_2$): δ 9.06 to 9.04 (m, 2H), 8.88 (s, 2H), 8.47 (s, 2H), 8.43 to 8.41 (m, 2H), 8.02 to 7.97 (m, 4H), 7.90 (dd, J=7.6, 0.8 Hz, 2H), 6.92 (dt, J=7.6, 1.2 Hz, 2H), 6.70 (dt, J=7.6, 1.2 Hz, 2H), 5.81 (dd, J=7.6, 0.8 Hz, 2H), 3.52 (s, 6H); $^{19}$F NMR (376 MHz, CDCl$_3$): 6-59.8 (s, 6F, 2CF$_3$), −72.65 (d, J=707 Hz, 6F, PF$_6^-$).

Example 19

Preparation of Compound (I-58):

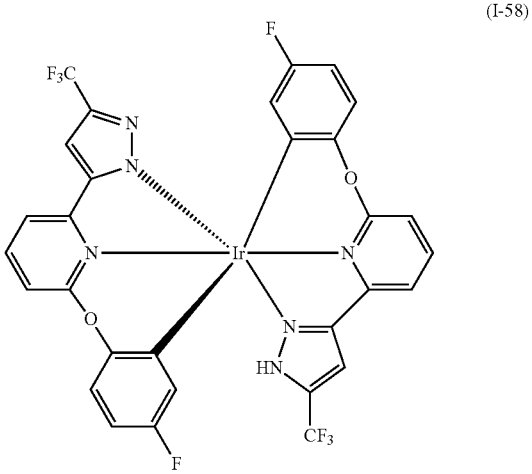

(I-58)

The synthesis steps of compound (I-55) were similar to those of compound (I-1), except that 2-(5-trifluoromethyl-1H-pyrazol-3-yl)-6-phenylpyridine was replaced by 2-(5-trifluoromethyl-1H-pyrazol-3-yl)-6-(4-fluorophenoxy)pyridine. A product was then obtained, with a yield of 55%.

Spectral data of compound (I-58): $^1$H NMR (400 MHz, CDCl$_3$): δ 7.94 (t, J=8.0 Hz, 2H), 7.55 (d, J=7.4 Hz, 2H), 7.19 (d, J=8.0 Hz, 2H), 6.91 (s, 2H), 6.88 to 6.84 (m, 2H), 6.43 to 6.38 (m, 2H), 5.51~5.48 (m, 2H); $^{19}$F NMR (376 MHz, CDCl$_3$): δ −60.84 (s, 6F); MS [FAB]: m/z 836.1, M$^+$.

Figure 2:
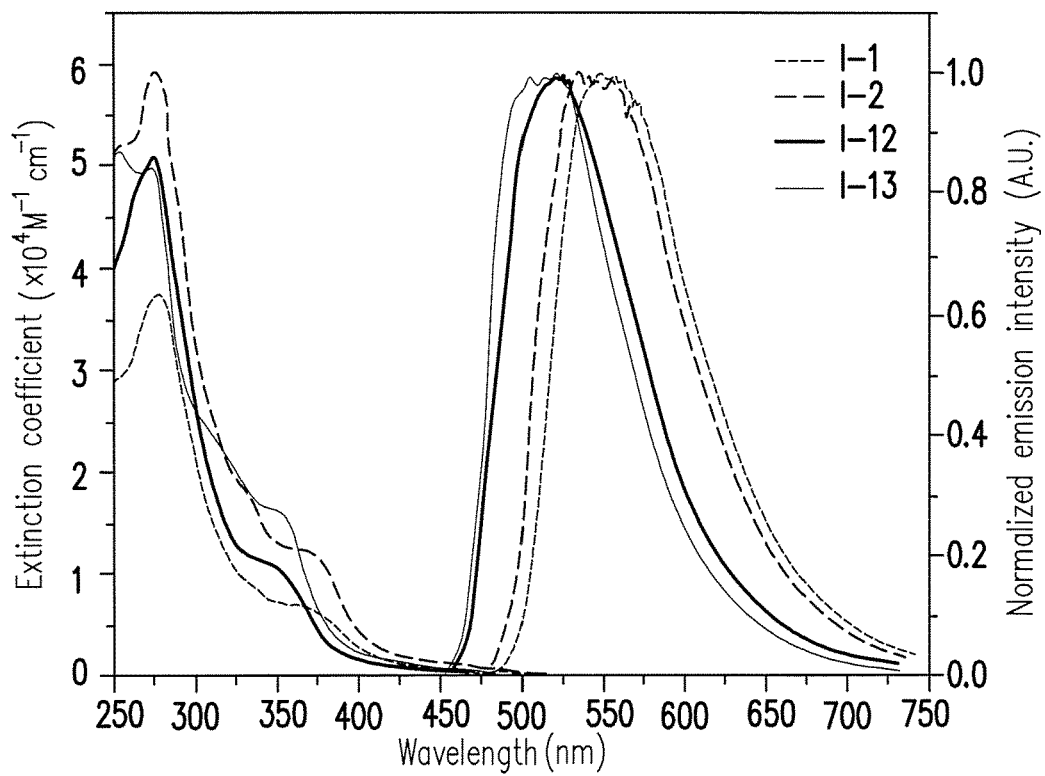
FIG. 2 shows the absorption spectrum and the emission spectrum of each of compounds (I-1), (I-2), (I-12), and (I-13) synthesized in examples 1, 2, 4, and 5 of the invention.

The absorption spectrum and the emission spectrum of each of compounds (I-1), (I-2), (I-12), and (I-13) synthesized in examples 1, 2, 4, and 5 are shown in FIG. 2, and the absorption peak location (abs λ$_{max}$), emission peak location (PL), quantum yield (Q.Y. %), and emission lifetime (τ$_{obs}$) thereof are shown in Table 1 below.

TABLE 1

| Compound | abs λ$_{max}$/nm (ε × 10$^4$ M$^{-1}$cm$^{-1}$)$^a$ | PL/nm$^b$ | Q.Y.%$^{b,c}$ | τ$_{obs}$/μs$^b$ |
|---|---|---|---|---|
| (I-1) | 278 (3.52), 370 (0.97) | 567 | 16 | 0.75 |
| (I-2) | 278 (5.61), 370 (1.13) | 545 | 57 | 2.07 |
| (I-12) | 275 (5.06), 352 (1.05) | 524 | 19 | 0.96 |
| (I-13) | 276 (4.87), 353 (1.58) | 525 | 37 | 0.90 |

$^a$Measured in CH$_2$Cl$_2$, with a concentration of 10$^{-5}$M.
$^b$Measured in a degassed CH$_2$Cl$_2$ solution.
$^c$Measured by using coumarin (C153) in ethanol (Q.Y. = 58%, λ$_{max}$ = 530 nm) as standard.

It can be known from FIG. 2 and Table 1 that, since compounds (I-1), (I-2), (I-12), and (I-13) have strong rigidity and high stability, the luminous efficiencies thereof are excellent. Moreover, compounds (I-1), (I-2), (I-12), and (I-13) are easily synthesized and are convenient to purify, and are therefore suitable for commercial production.

Figure 3:
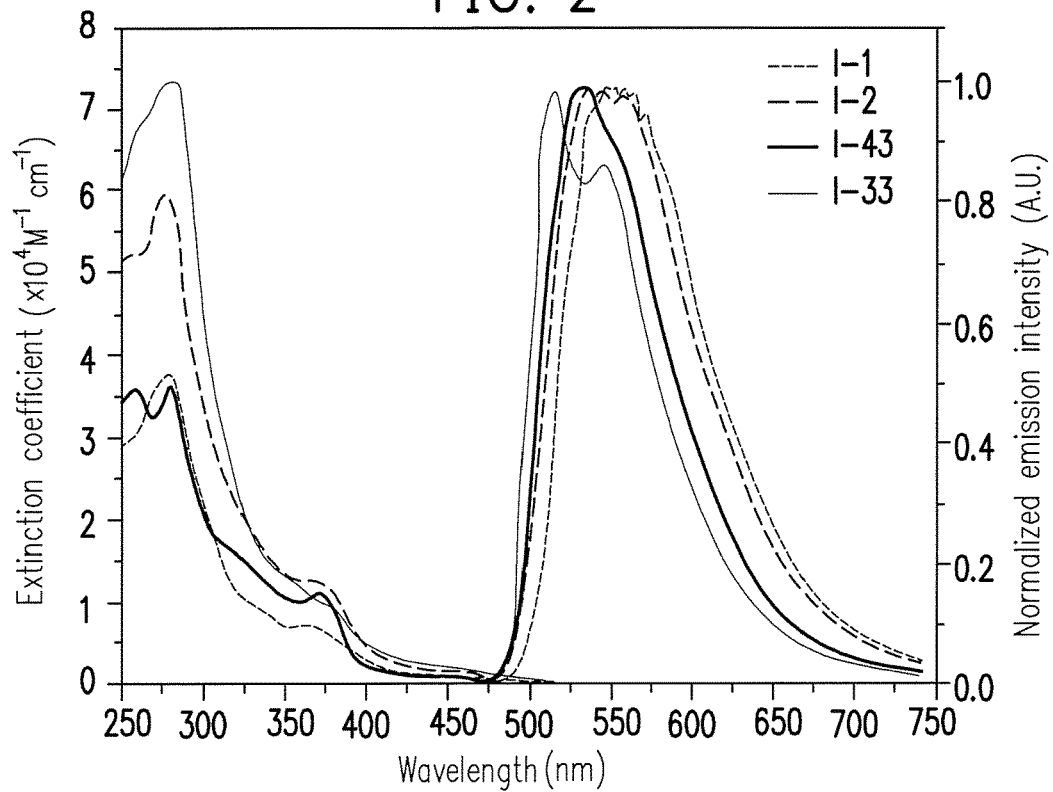
FIG. 3 shows the absorption spectrum and the emission spectrum of each of compounds (I-1), (I-2), (I-33), and (I-43) synthesized in examples 1, 2, 13, and 16 of the invention.

The absorption spectrum and the emission spectrum of each of compounds (I-1), (I-2), (I-33), and (I-43) synthesized in examples 1, 2, 13, and 16 are shown in FIG. 3, and the absorption peak location (abs λ$_{max}$), emission peak location (PL), quantum yield (Q.Y. %), and emission lifetime ($\tau_{obs}$) are shown in Table 2 below.

TABLE 2

| Compound | abs $\lambda_{max}$/nm ($\epsilon \times 10^4$ M$^{-1}$cm$^{-1}$)$^a$ | PL/nm$^b$ | Q.Y.%$^{b,c}$ | $\tau_{obs}$/µs$^b$ |
|---|---|---|---|---|
| (I-1) | 278 (3.52), 370 (0.97) | 567 | 16 | 0.75 |
| (I-2) | 278 (5.61), 370 (1.13) | 545 | 57 | 2.07 |
| (I-33) | 258 (5.87), 369 (0.99) | 517, 547 | 86 | 2.02 |
| (I-43) | 278 (5.31), 371 (1.04) | 531 | 76 | 3.00 |

$^a$Measured in CH$_2$Cl$_2$, with a concentration of 10$^{-5}$M.
$^b$Measured in a degassed CH$_2$Cl$_2$ solution.
$^c$Measured by using coumarin (C153) in ethanol (Q.Y. = 58%, $\lambda_{max}$ = 530 nm) as standard.

It can be known from FIG. 3 and Table 2 that, since compounds (I-1), (I-2), (I-33), and (I-43) have strong rigidity and high stability, the luminous efficiencies thereof are excellent. The positively charged compound (I-43) and the negatively charged compound (I-33) also have better water-solubility, and can be applied in the medical field upon modification with biological functional groups.

The absorption peak location (abs $\lambda_{max}$), emission peak location (PL), quantum yield (Q.Y. %), and emission lifetime ($\tau_{obs}$) of the absorption and emission of each of compounds (I-1), (I-2), (I-12), (I-13), (I-17), (I-18), (I-20), (I-21), (I-25), (I-33), (I-35), (I-36), (I-49), (I-50), (I-55) synthesized in the examples of the invention are shown in Table 3 below.

TABLE 3

| Compound | abs $\lambda_{max}$/nm ($\epsilon \times 10^4$ M$^{-1}$cm$^{-1}$)$^a$ | PL/nm$^b$ | Q.Y.%$^{b,c}$ | $\tau_{obs}$/µs$^b$ |
|---|---|---|---|---|
| (I-1) | 279 (3.52), 370 (0.97) | 567 | 16 | 0.75 |
| (I-2) | 278 (5.61), 370 (1.13) | 545 | 57 | 2.07 |
| (I-12) | 275 (5.06), 352 (1.05) | 524 | 19 | 0.96 |
| (I-13) | 276 (4.87), 353 (1.58) | 525 | 37 | 0.90 |
| (I-17) | 254 (0.79), 278 (0.65), 362 (0.18) | 580 | 37 | 1.09 |
| (I-18) | 257 (0.99), 284 (0.99), 370 (0.24) | 595 | 28 | 0.66 |
| (I-20) | 308 (4.79), 380 (1.97), 479 (0.30) | 638, 673 | 66 | 1.71 |
| (I-21) | 310 (5.30), 382 (2.25), 481 (0.34) | 646, 696 | 50 | 1.18 |
| (I-25) | 260 (1.01), 309 (0.93), 379 (0.43) | 645, 692 | 46 | 1.79 |
| (I-33) | 258 (5.87), 369 (0.99) | 517, 547 | 86 | 2.02 |
| (I-35) | 254 (0.72), 286 (0.60), 352 (0.22) | 540 | 85 | 3.87 |
| (I-36) | 253 (0.62), 319 (0.51), 362 (0.28) | 617, 664 | 94 | 2.79 |
| (I-49) | 302 (2.21), 361 (1.31)), 477 (0.21) | 550 | 40 | 1.11 |
| (I-50) | 308 (5.02), 372 (2.75), 479 (0.30) | 630, 683 | 45 | 1.73 |
| (I-55) | 257 (3.57), 279 (3.62), 373 (1.09) | 531 | 80 | 11.9 |

$^a$Measured in CH$_2$Cl$_2$, with a concentration of 10$^{-5}$M.
$^b$Measured in a degassed solution.
$^c$Measured by using coumarin (C153) in ethanol (Q.Y. = 58%, $\lambda_{max}$ = 530 nm) as standard.

Figure 4:
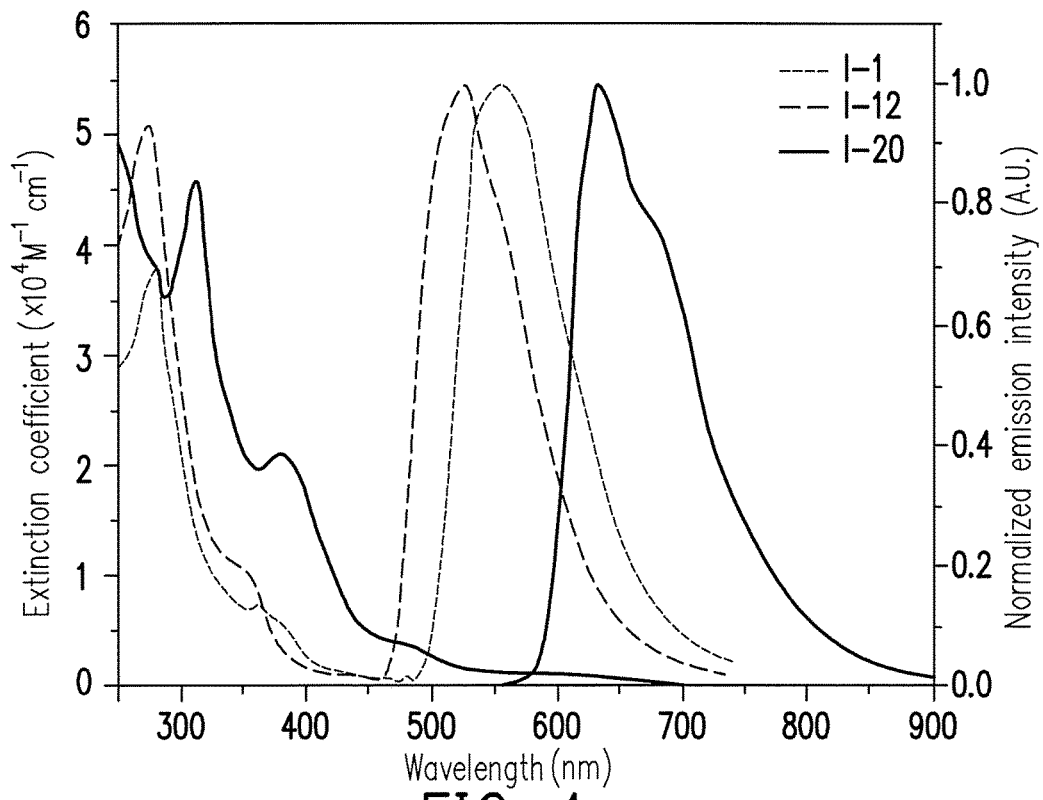
FIG. 4 shows the absorption spectrum and the emission spectrum of each of compounds (I-1), (I-12), and (I-20) synthesized in examples 1, 4, and 9 of the invention.

The absorption spectrum and the emission spectrum of each of compounds (I-1), (I-12), and (I-20) are shown in FIG. 4. Compounds (I-1), (I-12), and (I-20) are all neutral iridium complexes in which R$^2$ is hydrogen. It can be known from FIG. 4 and Table 3 that, compounds (I-1), (I-12), and (I-20) have strong rigidity and high stability, and therefore have excellent luminous efficiency.

Figure 5:
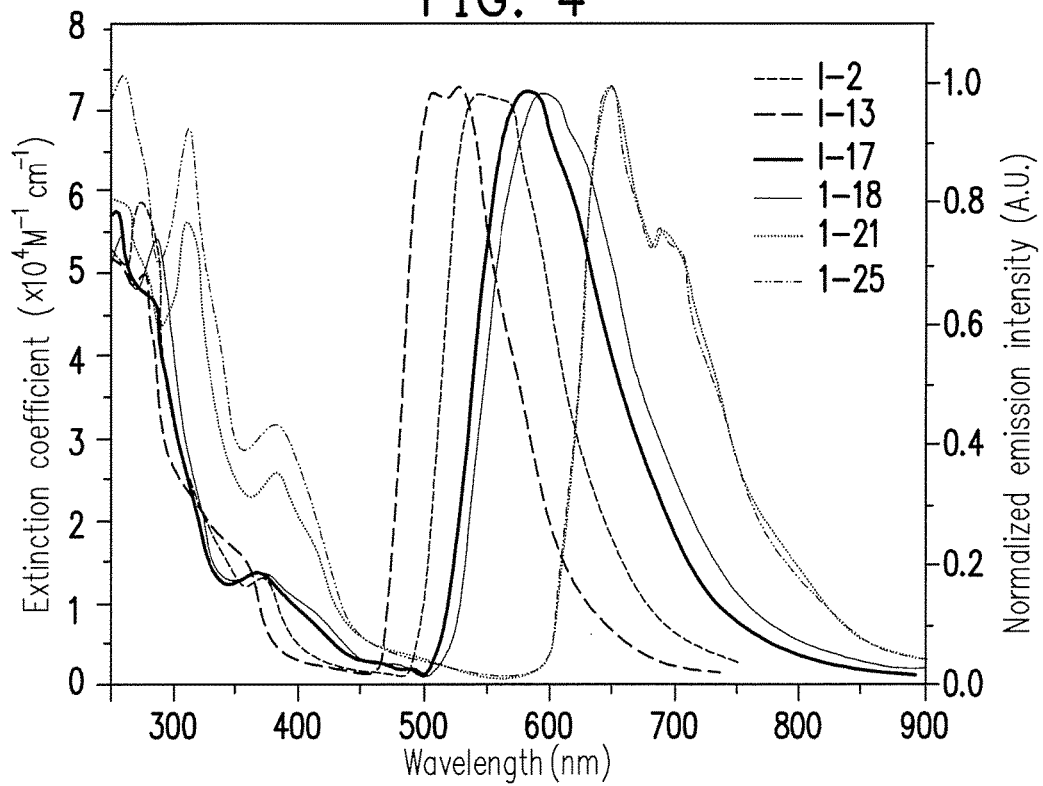
FIG. 5 shows the absorption spectrum and the emission spectrum of each of compounds (I-2), (I-13), (I-17), (I-18), (I-21), and (I-25) synthesized in examples 2, 5, 7, 8, 10, and 12 of the invention.

The absorption spectrum and the emission spectrum of each of compounds (I-2), (I-13), (I-17), (I-18), (I-21), and (I-25) are shown in FIG. 5. Compounds (I-2), (I-13), (I-17), (I-18), (I-21), and (I-25) are all neutral iridium complexes in which R$^2$ is methyl. It can be known from FIG. 5 and Table 3 that, compounds (I-2), (I-13), (I-17), (I-18), (I-21), and (I-25) have strong rigidity and high stability, and therefore have excellent luminous efficiency.

Figure 6:
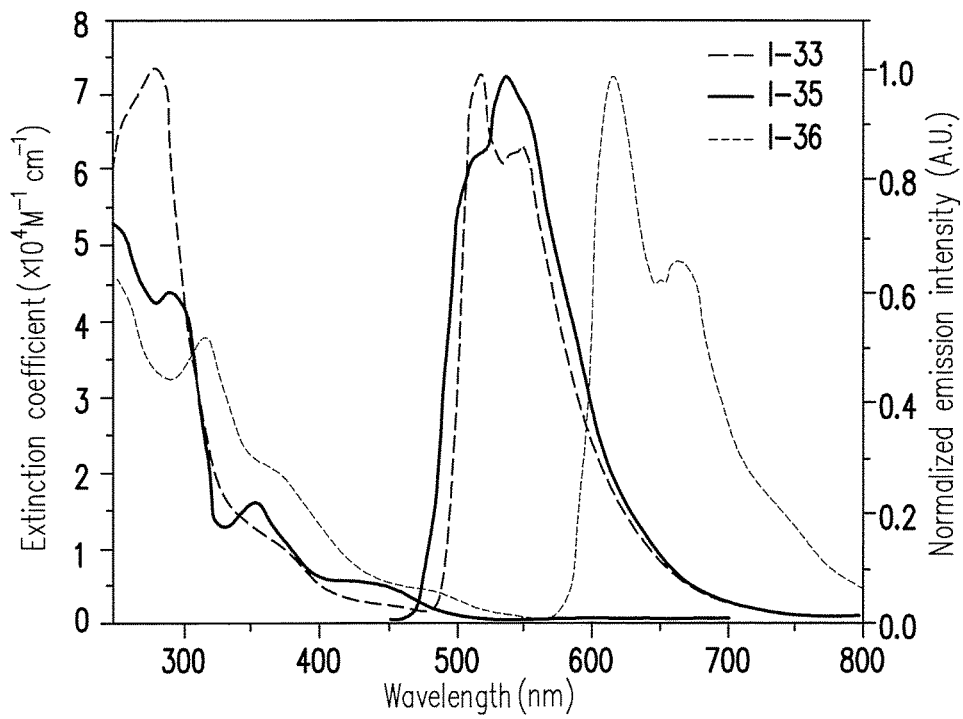
FIG. 6 shows the absorption spectrum and the emission spectrum of each of compounds (I-33), (I-35), and (I-36) synthesized in examples 13, 14, and 15 of the invention.

The absorption spectrum and the emission spectrum of each of compounds (I-33), (I-35), and (I-36) are shown in FIG. 6. Compounds (I-33), (I-35), and (I-36) are all negatively charged iridium complexes. It can be known from FIG. 6 and Table 3 that, compounds (I-33), (I-35), and (I-36) have strong rigidity and high stability, and therefore have excellent luminous efficiency. Compounds (I-33), (I-35), and (I-36) also have better water-solubility, and can be applied in the medical field upon modification with biological functional groups.

Figure 7:
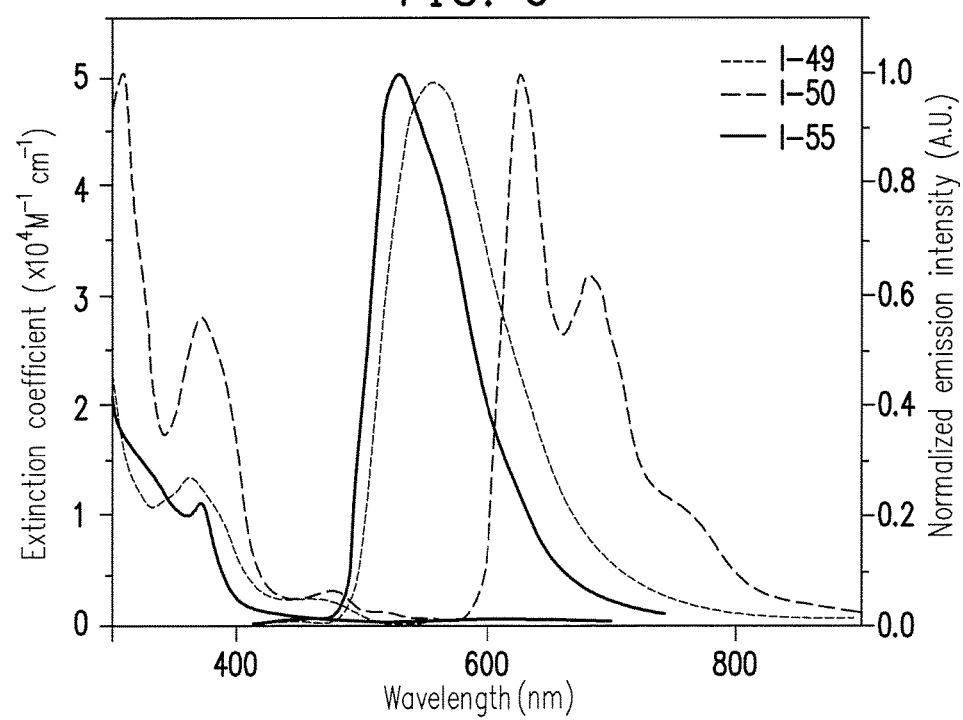
FIG. 7 shows the absorption spectrum and the emission spectrum of each of compounds (I-49), (I-50), and (I-55) of the invention.

The absorption spectrum and the emission spectrum of each of compounds (I-49), (I-50), and (I-55) are shown in FIG. 7. Compounds (I-49), (I-50), and (I-55) are all positively charged iridium complexes, and it can be known from FIG. 7 and Table 3 that, compounds (I-49), (I-50), and (I-55) have strong rigidity and high stability, and therefore have excellent luminous efficiency. Compounds (I-49), (I-50), and (I-55) also have better water-solubility, and can be applied in the medical field upon modification with biological functional groups.

Moreover, the above compounds are easily synthesized and are convenient to purify, the yield of all the compounds reaches 40% or more, and the yield of a portion of the compounds even reaches 70% or 80% or more. In other words, the compounds of the invention are suitable for commercial production.

In the above embodiments, although the iridium complex of general formula (I) is used as an example, the invention is not limited thereto. Those having ordinary skill in the art should understand that, as long as a complex is formed by the reaction of iridium (III) metal and a ligand precursor with proton transfer capability, such complex is within the scope of the invention. In other words, the spirit of the invention is that by reacting iridium (III) metal and a ligand precursor with proton transfer capability, a complex with iridium (III) metal can be formed by using a single type or two types of ligands which have substantially the same main structure but carry different valence states or formal charges.

For instance, the iridium complex can be represented by general formula (III) below:

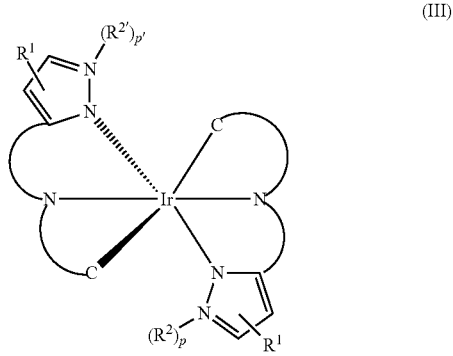

(III)

wherein R$^1$ is substituted or unsubstituted C$_1$-C$_{12}$ alkyl, substituted or unsubstituted C$_6$-C$_{12}$ aryl, or —C$_m$F$_{2m+1}$, m is an integer of 0 to 3; R$^2$ is hydrogen, C$_1$-C$_6$ alkyl, substituted or unsubstituted $C_1$-$C_{12}$ alkyl, or substituted or unsubstituted $C_6$-$C_{12}$ aryl; and p and p' are each independently 0 or 1.

The iridium complex of the invention can be applied in OLED. In an embodiment, the OLED includes two electrodes and a light-emitting layer disposed between the two electrodes, and the light-emitting layer contains at least one iridium complex of the invention. For instance, the iridium complex of the invention is used as a dopant and is doped into a host material of the light-emitting layer.

Based on the above, the bis-tridentate iridium complex of the invention has strong rigidity and high stability, and can therefore increase luminous efficiency. The iridium complex of the invention is easily synthesized, is convenient to purify, and has a high yield, and is therefore suitable for commercial production. Moreover, the structure of the iridium complex of the invention can also be modified via a simple reaction to change the valence state or formal charge thereof. The iridium complex having a neutral valence state or zero formal charge can be used in fabrication of OLED using thermal vacuum deposition. The complex having a positive or negative valence state is water-soluble and can be modified with biological functional groups, and accordingly can be applied in the medical field. Therefore, the application of the iridium complex of the invention is very broad.

Although the invention has been described with reference to the above embodiments, it will be apparent to one of ordinary skill in the art that modifications to the described embodiments may be made without departing from the spirit of the invention. Accordingly, the scope of the invention is defined by the attached claims not by the above detailed descriptions.

What is claimed is:

1. An iridium complex represented by general formula (I):

(I)

wherein

R$^1$ and R$^{1'}$ are each independently substituted or unsubstituted $C_1$-$C_{12}$ alkyl, substituted or unsubstituted $C_6$-$C_{12}$ aryl, or —$C_mF_{2m+1}$, and m is an integer of 0 to 3;

R$^2$ and R$^{2'}$ are each independently hydrogen, substituted or unsubstituted $C_1$-$C_{12}$ alkyl, or substituted or unsubstituted $C_6$-$C_{12}$ aryl;

p and p' are each independently 0 or 1;

R$^3$, R$^{3'}$, R$^4$, and R$^{4'}$ are each independently hydrogen, fluorine, substituted or unsubstituted $C_1$-$C_{12}$ alkyl, substituted or unsubstituted $C_1$-$C_6$ alkoxyl, or substituted or unsubstituted $C_6$-$C_{12}$ aryl;

q and q' are each independently an integer of 0 to 3;

r and r' are each independently an integer of 0 to 4;

$X^1$, $X^2$, $X^3$, $X^4$, $X^5$, $X^6$, and $X^7$ are each independently carbon or nitrogen;

A is —O—, —$CH_2$—, or —$CR_2$—, and R is methyl, ethyl, or propyl;

a is 0 or 1;

when q is equal to or greater than 2, each R$^3$ can be the same or different, and two or more R$^3$'s can joint to form a $C_3$-$C_8$ aromatic ring;

when q' is equal to or greater than 2, each R$^{3'}$ can be the same or different, and two or more R$^{3'}$'s can joint to form a $C_3$-$C_8$ aromatic ring;

when r is equal to or greater than 2, each R$^4$ can be the same or different, and two or more R$^4$'s can joint to form a $C_3$-$C_8$ aromatic ring; and when r' is equal to or greater than 2, each R$^{4'}$ can be the same or different, and two or more R$^{4'}$'s can joint to form a $C_3$-$C_8$ aromatic ring.

2. The iridium complex of claim 1, wherein a bonding site of R$^{1'}$ of a left ligand is the same as a bonding site of R$^1$ of a right ligand, and R$^{1'}$ and R$^1$ have the same structure, a bonding site of R$^{3'}$ of the left ligand is the same as a bonding site of R$^3$ of the right ligand, and R$^{3'}$ and R$^3$ have the same structure, and a bonding site of R$^{4'}$ of the left ligand is the same as a bonding site of R$^4$ of the right ligand, and R$^{4'}$ and R$^4$ have the same structure.

3. The iridium complex of claim 1, wherein a is 0.

4. The iridium complex of claim 1, wherein the iridium complex is electrically neutral.

5. The iridium complex of claim 4, wherein one of p and p' is 1, and the other of p and p' is 0.

6. The iridium complex of claim 5, having a structure selected from one of formula (I-1) to formula (I-32) and formula (I-32-a) to formula (I-32-b):

I-1

-continued
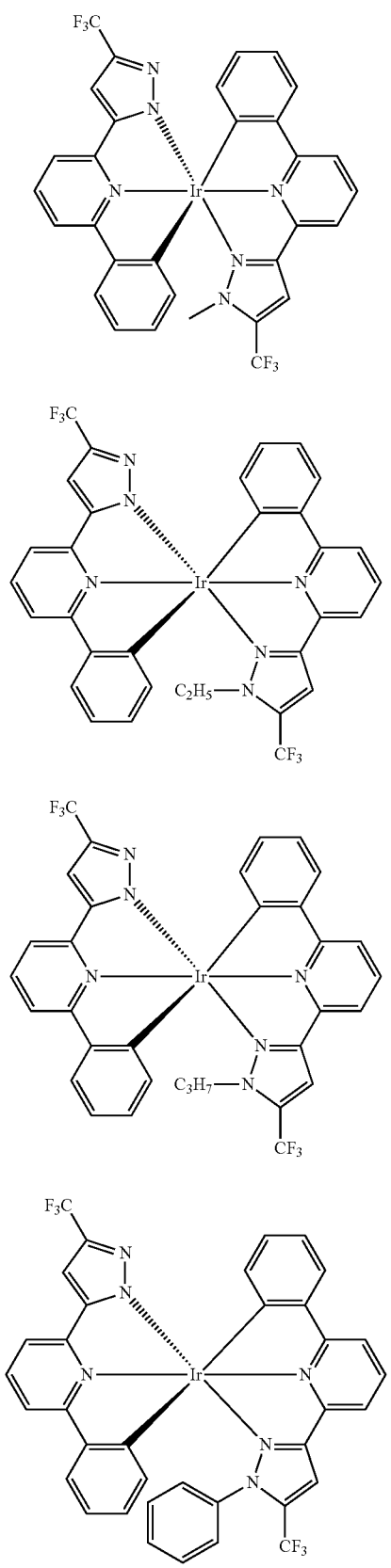
I-2
I-3
I-4
I-5
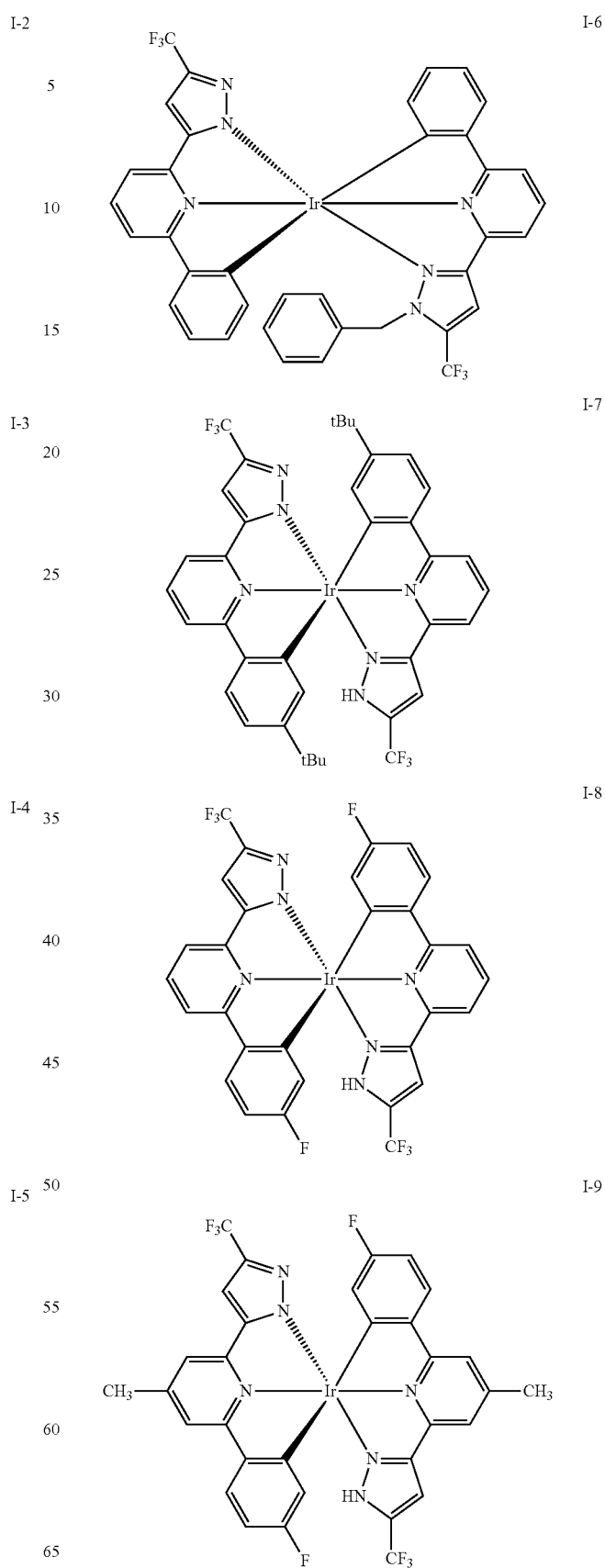
I-6
I-7
I-8
I-9

I-10
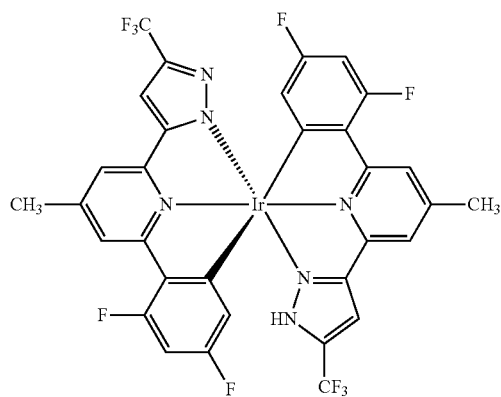
I-11
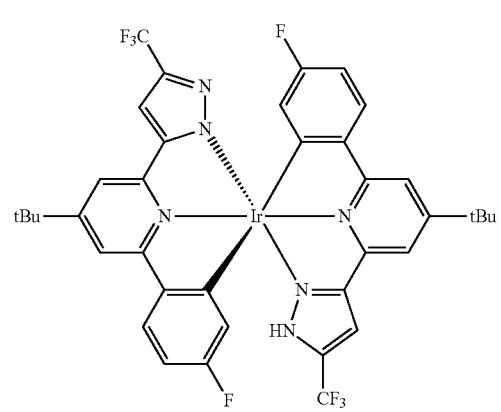
I-12
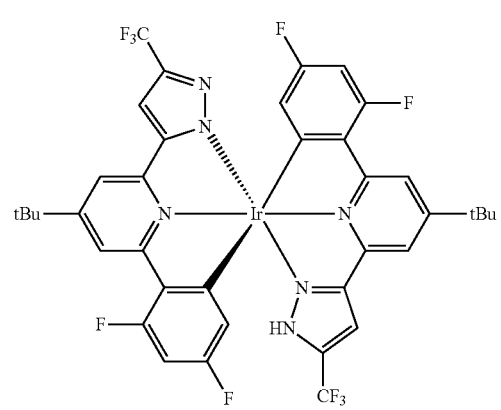
I-13
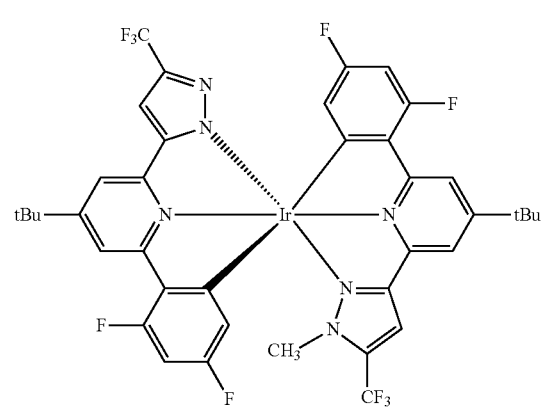
I-14
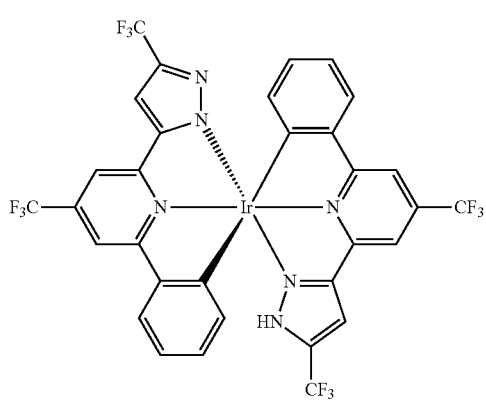
I-15
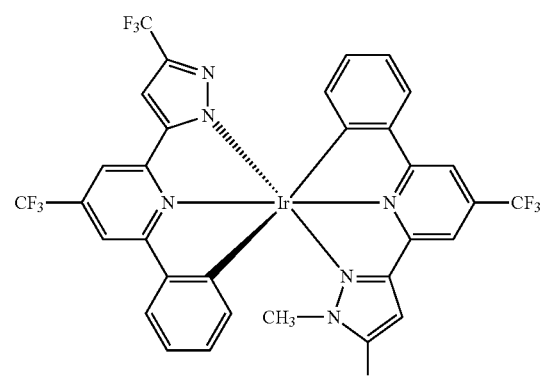
I-16
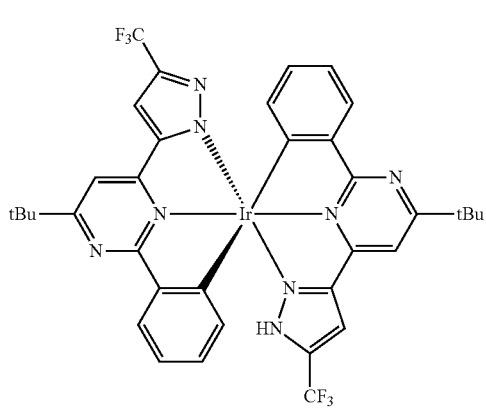

-continued
I-17
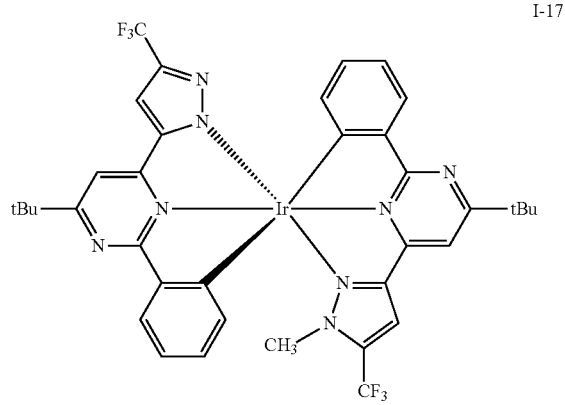
I-18
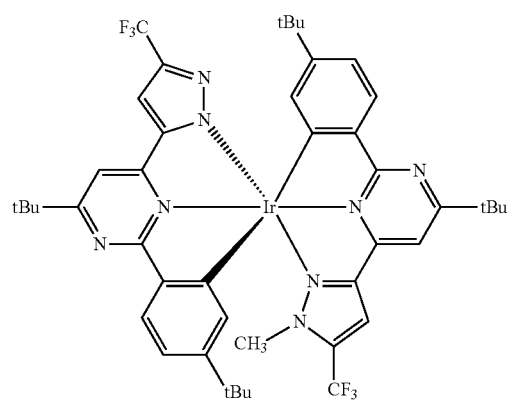
I-19
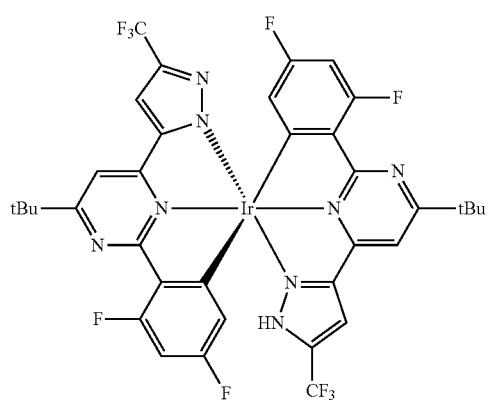
I-20
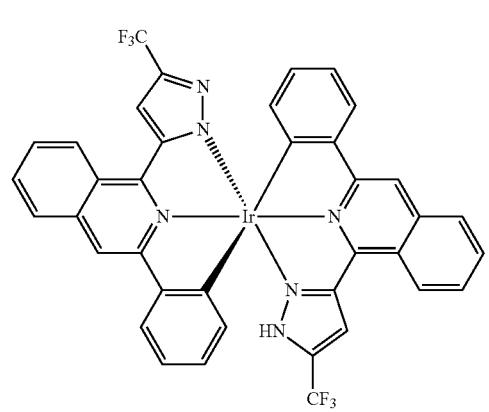
-continued
I-21
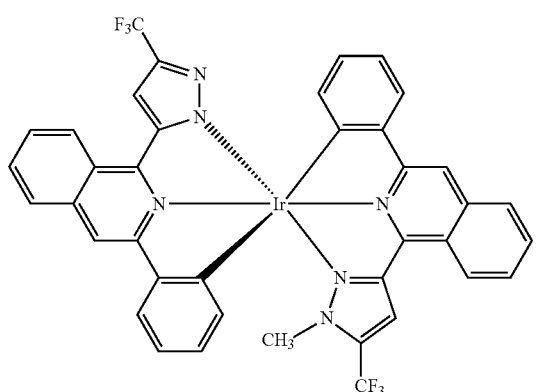
I-22
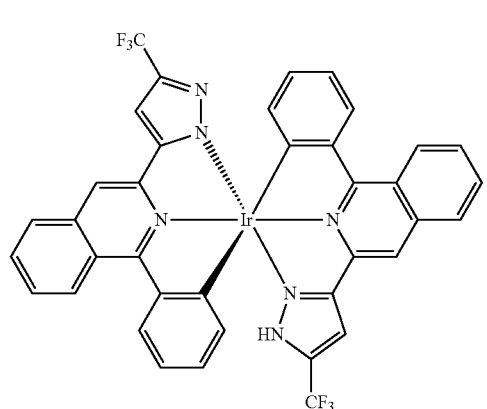
I-23
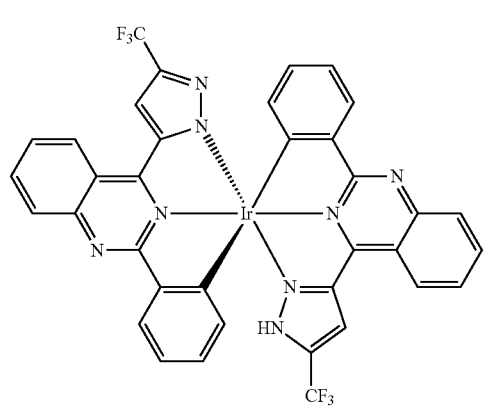
I-24
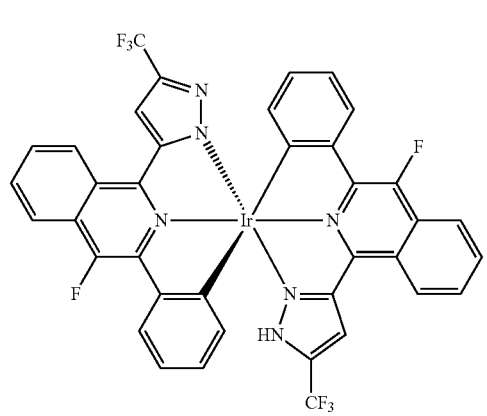

-continued
I-25
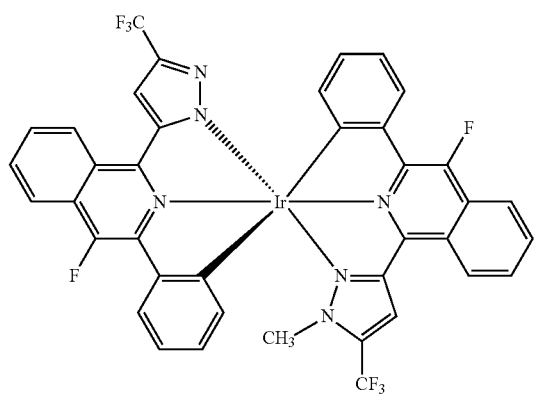
I-26
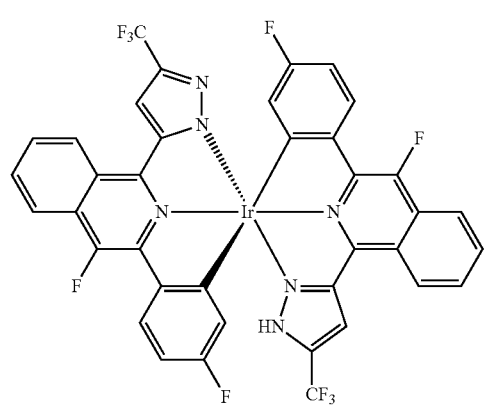
I-27
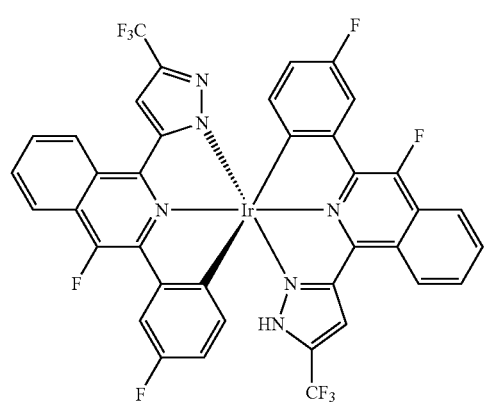
I-28
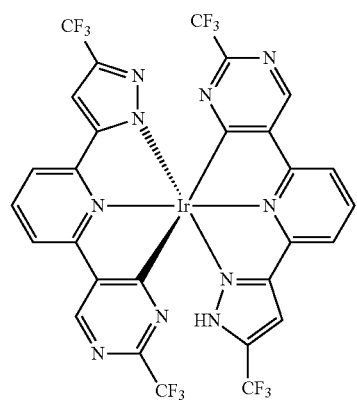
-continued
I-29
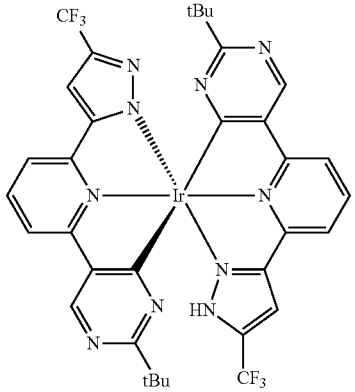
I-30
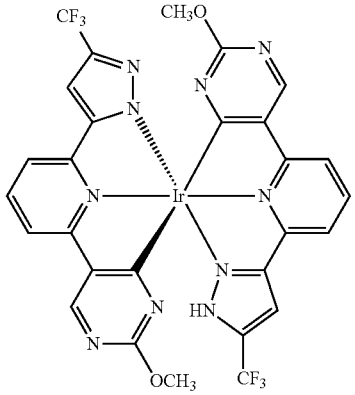
I-31
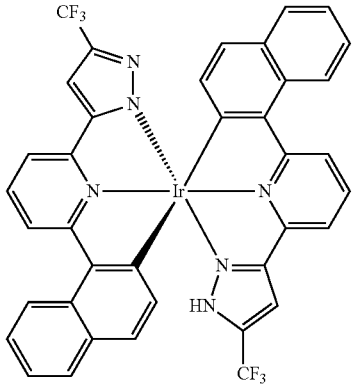
I-32
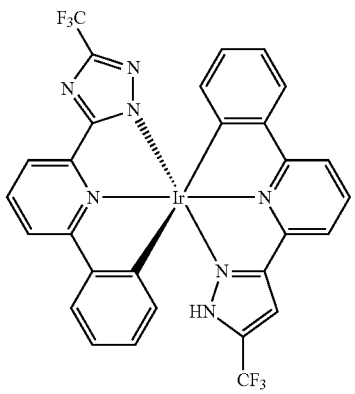

I-32-a
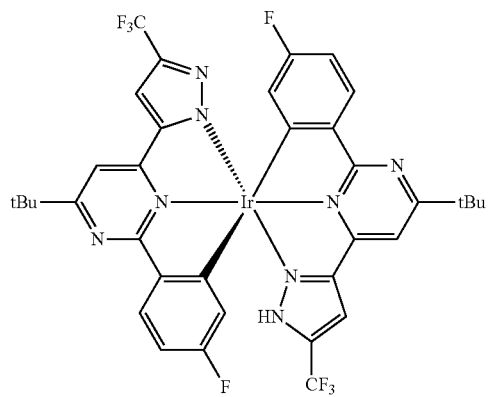
I-34
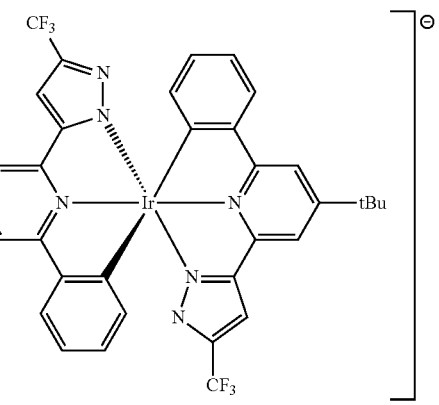
I-32-b
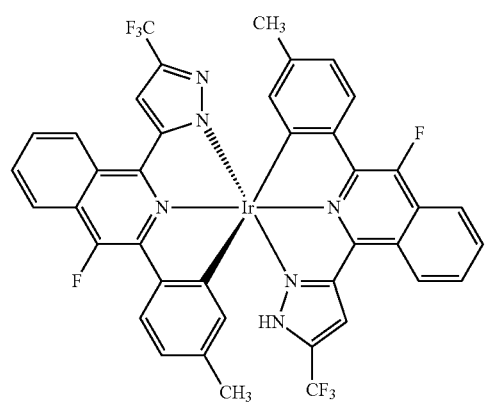
I-35
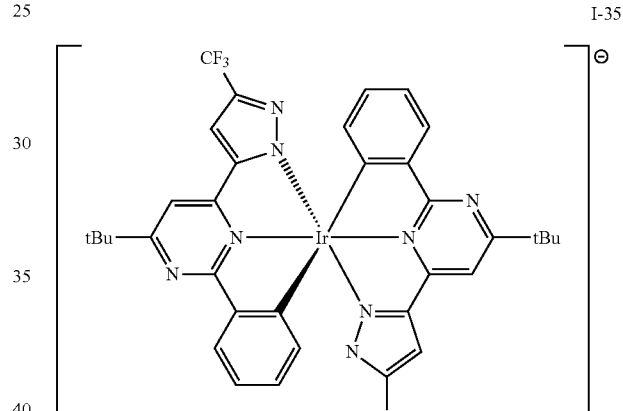
7. The iridium complex of claim 1, wherein the iridium complex is negatively charged.
8. The iridium complex of claim 7, wherein p and p' are 0.
9. The iridium complex of claim 8, having a structure selected from one of formula (I-33) to formula (I-42):
I-33
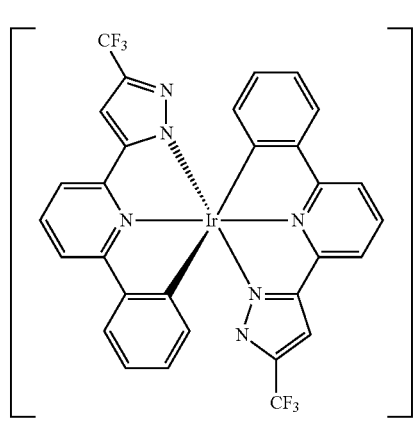
I-36
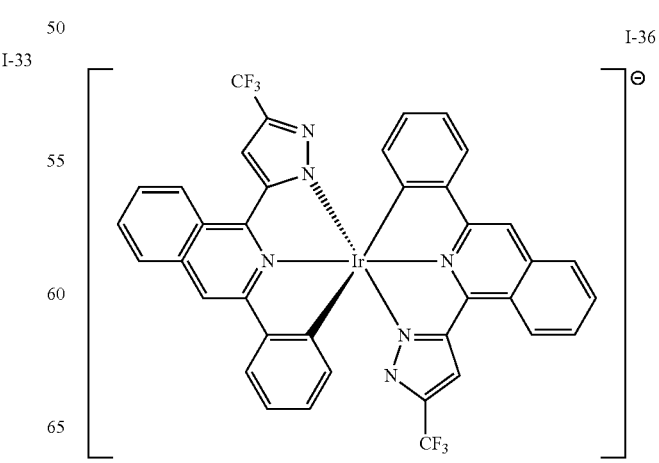

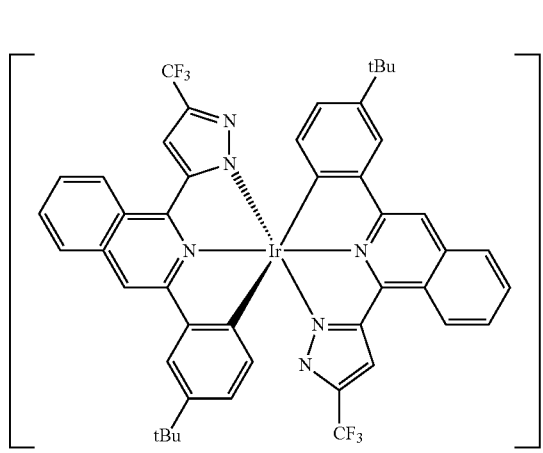
I-37
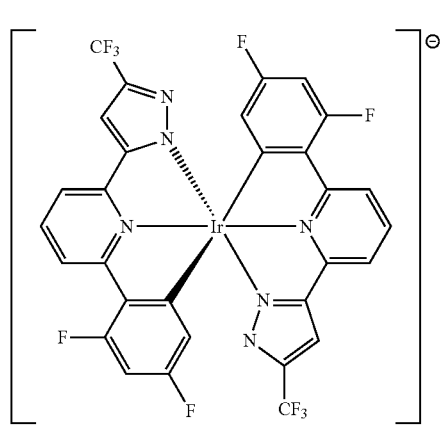
I-40
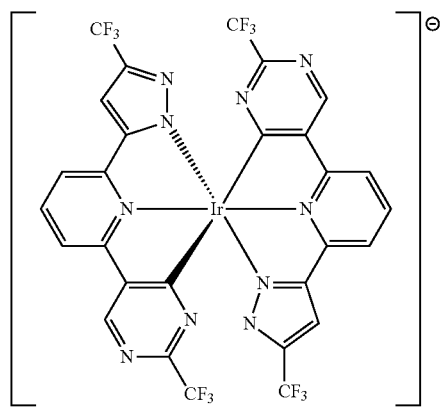
I-41
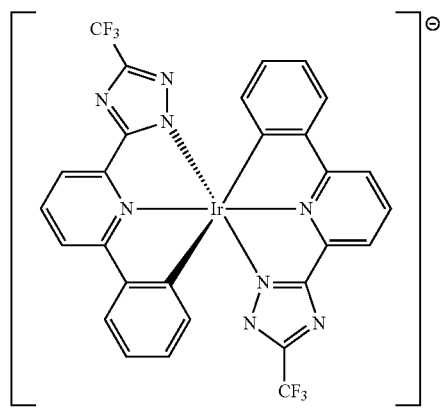
I-42
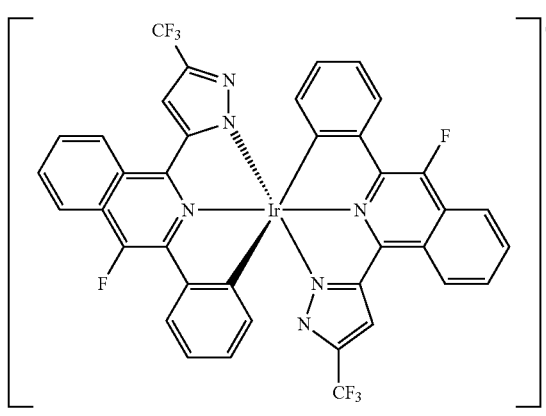
I-38
I-39
10. The iridium complex of claim 1, wherein the iridium complex is positively charged.
11. The iridium complex of claim 10, wherein p and p' are 1.
12. The iridium complex of claim 11, having a structure selected from one of formula (I-43) to formula (I-56):

I-43
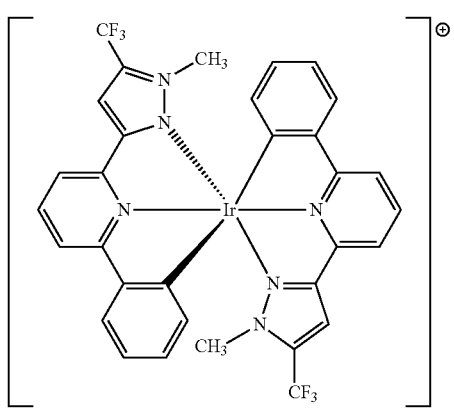
I-44
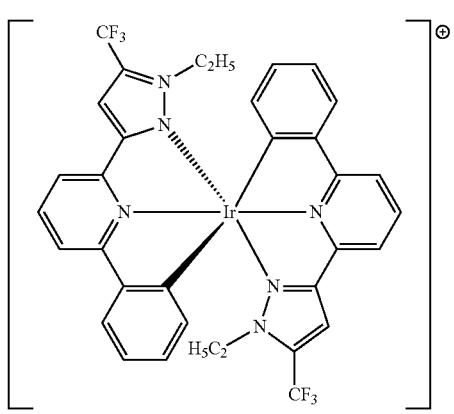
I-45
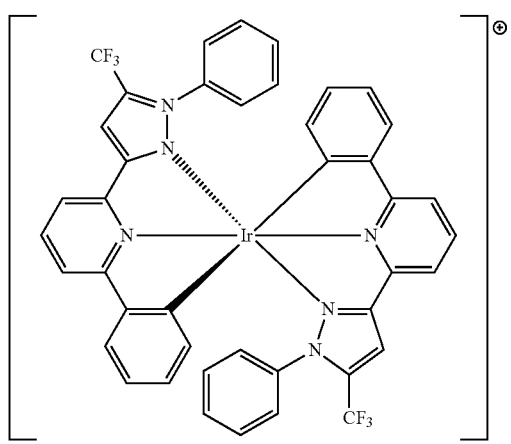
I-46
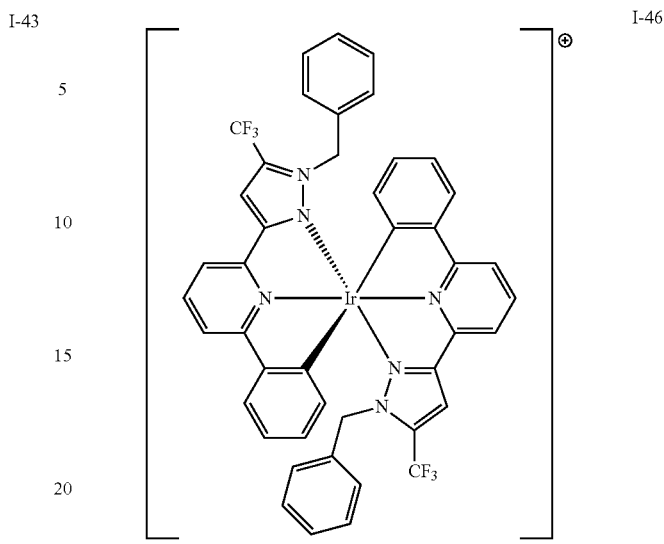
I-47
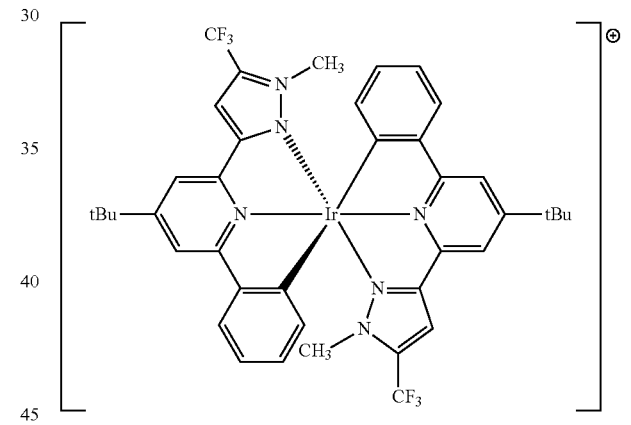
I-48
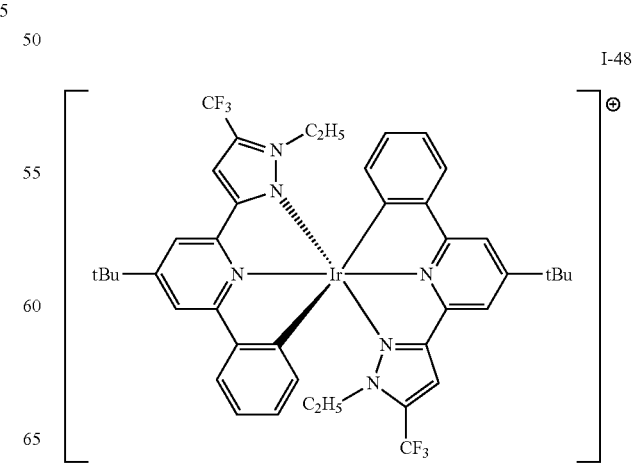

I-49
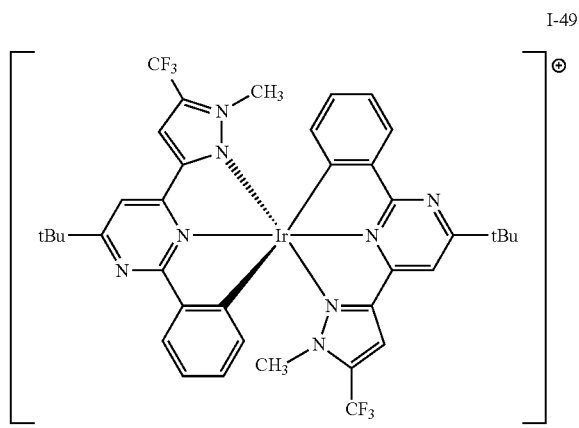
I-50
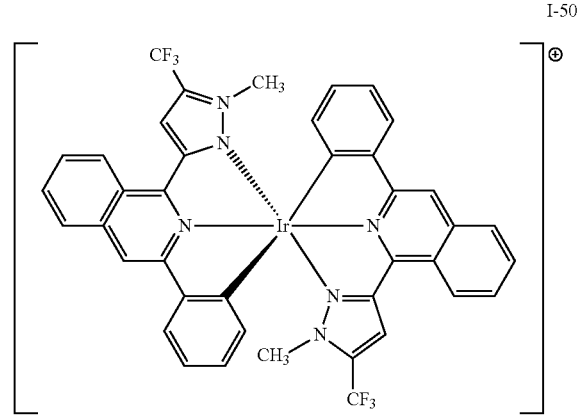
I-51
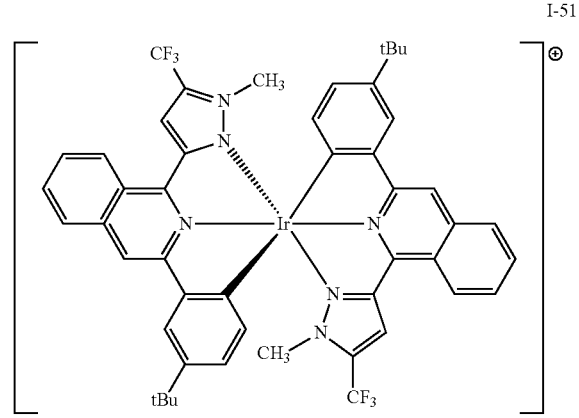
I-52
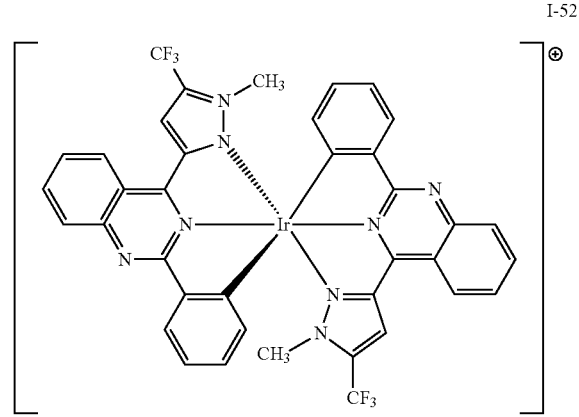
I-53
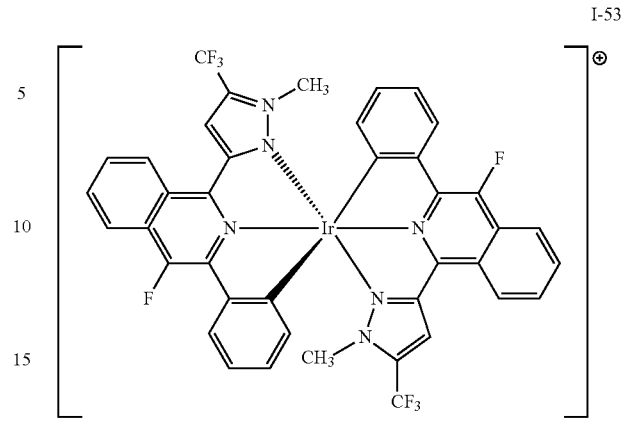
I-54
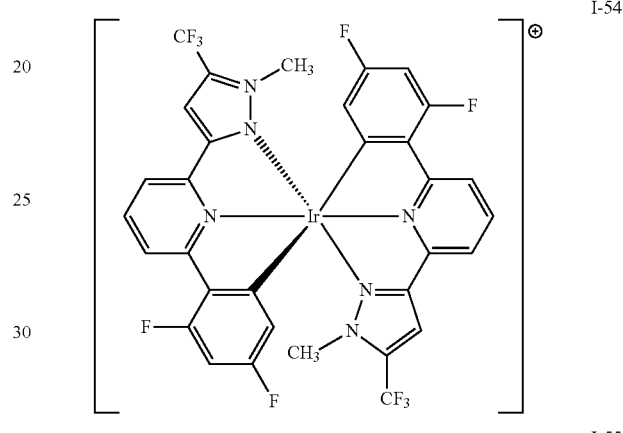
I-55
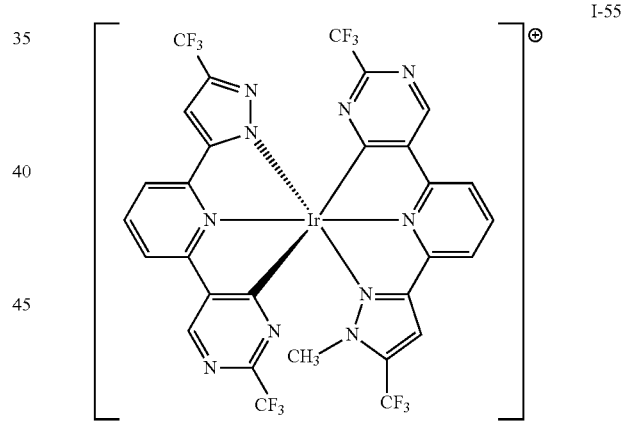
I-56
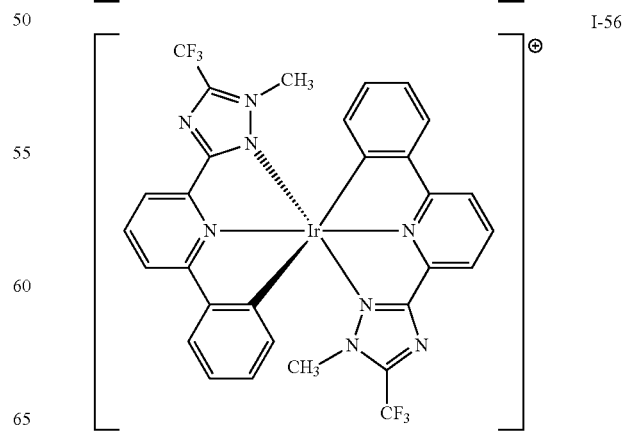

13. The iridium complex of claim 1, wherein a is 1.
14. The iridium complex of claim 13, wherein one of p and p' is 1, and the other of p and p' is 0.
15. The iridium complex of claim 14, having a structure selected from one of formula (I-57) to formula (I-64):
I-57
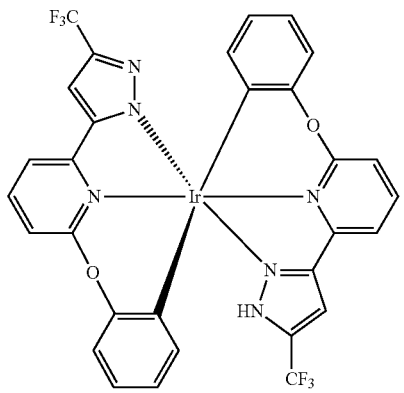
I-58
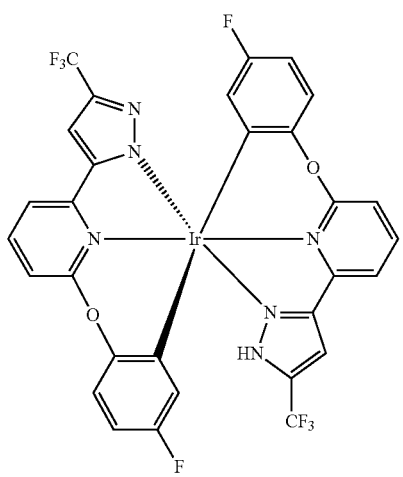
I-59
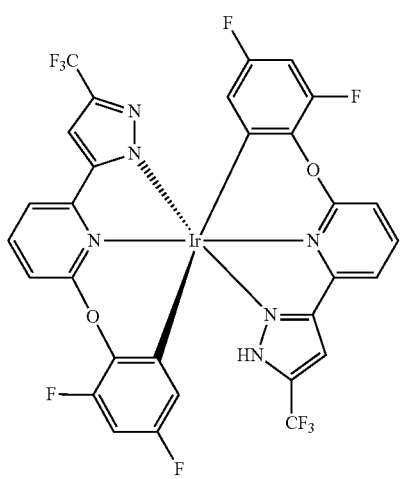
-continued
I-60
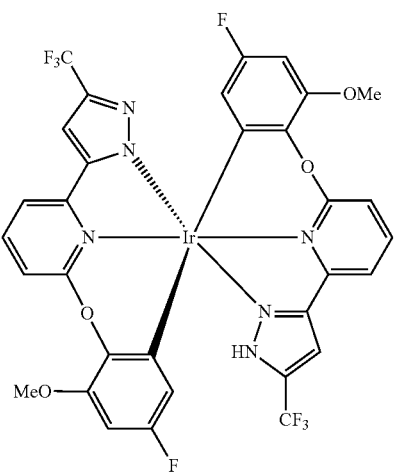
I-61
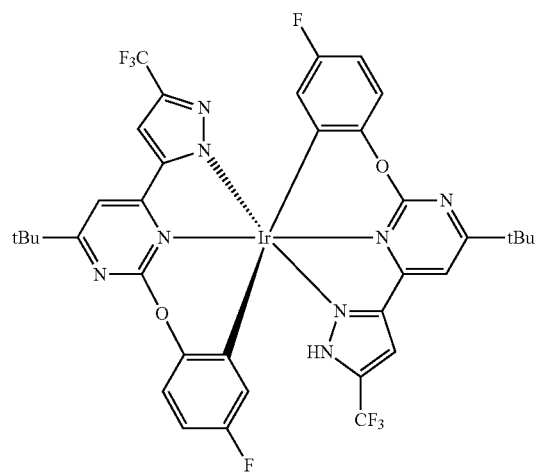
I-62
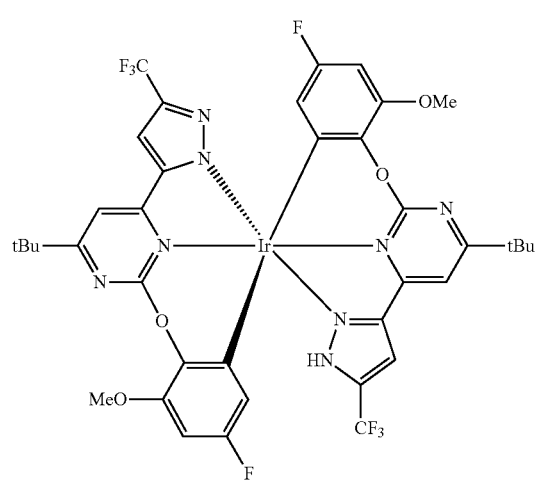

I-63
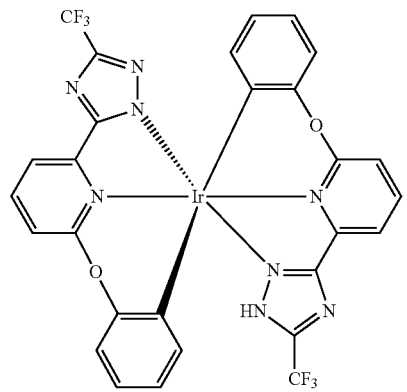
I-64
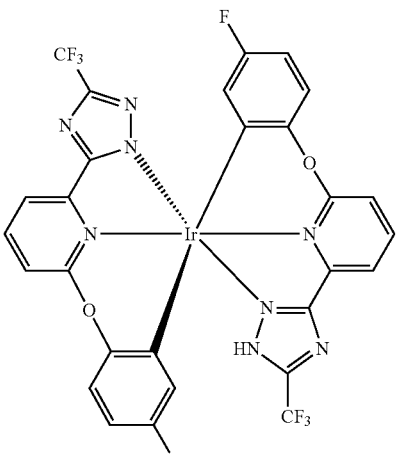
* * * * *